United States Patent
Rosen

(10) Patent No.: US 9,358,261 B2
(45) Date of Patent: Jun. 7, 2016

(54) ADDITIONAL ARTEMISININ AND BERBERINE COMPOSITIONS AND METHODS OF MAKING

(71) Applicant: U.S. Phytotherapy, Inc., Orlando, FL (US)

(72) Inventor: Bob Rosen, Orlando, FL (US)

(73) Assignee: U.S. Phytotherapy, Inc., Orlando, FL (US)

( * ) Notice: Subject to any disclaimer, the term of this patent is extended or adjusted under 35 U.S.C. 154(b) by 0 days.

(21) Appl. No.: 14/933,229

(22) Filed: Nov. 5, 2015

(65) Prior Publication Data

US 2016/0058809 A1    Mar. 3, 2016

Related U.S. Application Data

(60) Continuation-in-part of application No. 14/614,946, filed on Feb. 5, 2015, now Pat. No. 9,186,331, which is a division of application No. 13/660,553, filed on Oct. 25, 2012, now Pat. No. 9,011,892.

(60) Provisional application No. 61/550,969, filed on Oct. 25, 2011.

(51) Int. Cl.

| | |
|---|---|
| A61K 31/365 | (2006.01) |
| A61K 31/366 | (2006.01) |
| A61K 31/4741 | (2006.01) |
| A61K 31/4745 | (2006.01) |
| A61K 31/4375 | (2006.01) |
| A61K 9/00 | (2006.01) |
| A61K 9/56 | (2006.01) |
| B65B 1/00 | (2006.01) |
| A61K 36/185 | (2006.01) |
| A61K 31/165 | (2006.01) |
| A61K 45/06 | (2006.01) |

(52) U.S. Cl.
CPC ........... *A61K 36/185* (2013.01); *A61K 31/165* (2013.01); *A61K 31/366* (2013.01); *A61K 31/4745* (2013.01); *A61K 45/06* (2013.01)

(58) Field of Classification Search
CPC ........... A61K 2300/00; A61K 31/365; A61K 31/366; A61K 31/4741; A61K 31/4745; A61K 31/4375; A61K 9/00; A61K 9/0056; A61K 9/288; B65B 1/00
See application file for complete search history.

(56) References Cited

U.S. PATENT DOCUMENTS

| | | | |
|---|---|---|---|
| 4,749,708 A | 6/1988 | Maroko | |
| 4,761,417 A | 8/1988 | Maroko | |

(Continued)

FOREIGN PATENT DOCUMENTS

| | | |
|---|---|---|
| EP | 2289554 | 3/2011 |
| JP | 2009051803 | 3/2009 |

OTHER PUBLICATIONS

Goswami, et al., Anti-Helicobacter pylori potential of artemisinin and its derivatives, Antimicrobial Agents and Chemotherapy, 2012, pp. 4594-4607, vol. 56, No. 9.

(Continued)

*Primary Examiner* — Ernst V Arnold
(74) *Attorney, Agent, or Firm* — Brian S. Steinberger; Law Offices of Brian S. Steinberger, P.A.

(57) ABSTRACT

An Alternative ACT composition consisting of natural botanical active ingredients, all of which are GRAS (generally regarded as safe by the FDA). The novel Artemisinin Combination Therapy (ACT) consists of artemisinin and its derivatives, berberine, capsaicin, and papaya extract. The four active substances mixed with various selected excipient compounds to form a single pill, tablet or capsule for the treatment and prevention of chikungunya.

20 Claims, 5 Drawing Sheets

2. TODAY, how easy is it for you to bend, kneel, or stoop?

(56) References Cited

U.S. PATENT DOCUMENTS

| | | | |
|---|---|---|---|
| 4,980,344 | A | 12/1990 | Maroko |
| 5,153,178 | A | 10/1992 | Maroko |
| 5,225,427 | A | 7/1993 | Vanugopalan |
| 5,225,562 | A | 7/1993 | McChesney |
| 5,413,928 | A | 5/1995 | Weathers |
| 5,856,351 | A | 1/1999 | Zheng |
| 6,127,405 | A | 10/2000 | Kumar |
| 6,136,847 | A | 10/2000 | Posner |
| 6,160,004 | A | 12/2000 | Posner |
| 6,306,896 | B1 | 10/2001 | Scheiwe |
| 6,346,631 | B1 | 2/2002 | Jain |
| 6,461,603 | B2 | 10/2002 | Bentley |
| RE38,117 | E | 5/2003 | Zheng |
| 6,610,327 | B1 | 8/2003 | Bosche |
| 6,649,647 | B1 | 11/2003 | Haynes |
| 6,683,193 | B2 | 1/2004 | Bhakuni |
| 6,685,972 | B2 | 2/2004 | Kumar |
| 6,737,438 | B2 | 5/2004 | Singh |
| 6,750,356 | B1 | 6/2004 | Bhakuni |
| 6,906,098 | B2 | 6/2005 | Solaja |
| 6,906,205 | B2 | 6/2005 | Vennerstrom |
| 6,984,640 | B1 | 1/2006 | Haynes |
| 7,071,226 | B1 | 7/2006 | Singh |
| 7,098,242 | B2 | 8/2006 | Elsohly |
| 7,482,334 | B2 | 1/2009 | Frincke |
| 7,547,687 | B2 | 6/2009 | Reading |
| 7,915,223 | B2 | 3/2011 | Mor |
| 7,935,839 | B2 | 5/2011 | Frincke |
| 7,947,846 | B2 | 5/2011 | Frincke |
| 8,026,209 | B2 | 9/2011 | Gaillard |
| 2005/0148628 | A1 | 7/2005 | Muller |
| 2009/0098207 | A1 | 4/2009 | Malakhov |
| 2011/0206636 | A1 | 8/2011 | Sas |
| 2013/0072513 | A1 | 3/2013 | Colman |

OTHER PUBLICATIONS

Lee, et al., Berberine ameliorates TNBS-induced colitis by inhibiting lipid peroxidation, enterobacterial growth and NF-kB activation, European Journal of Pharmacology, 2010, pp. 162-170, vol. 648.

Li, et al., Berberine inhibits acute radiation intestinal syndrome in human with abdomen radiotherapy, Med Oncol, 2010, pp. 919-925, vol. 27.

Yan, et al., Berberine promotes recovery of colitis and inhibits inflammatory responses in colonic macrophages and epithelial cells in DSS-treated mice, Am J Physiol Gastrointest Liver Physiol, 2012, pp. G504-G514, vol. 302.

Zhang, et al., Evidence for the complementary and synergistic effects of the three-alkaloid combination regimen containing berberine, hypaconitine and skimmianine on the ulcertative colitis rats induced by trinitrobenzene-sulfonic acid, European Journal of Pharmacology, 2011, pp. 187-196, vol. 651.

Gofton, et al, Mefloquine in the treatment of progressive multifocal leukoencephalopathy, J Neurol Neurosurg Psychiatry, 2011, pp. 452-455, vol. 82.

Kawashima, et al., Pharmacological properties of traditional medicine (XXIX): effect of hange-shashin-to and the combinations of its herbal constituents on rat experimental colitis, Biol. Pharm. Bull, 2004, pp. 1599-1603, vol. 27, No. 10.

Act Rx: To save a life, 2012, http://actrxlimited.com/content/products, 2 pages.

Yarnell, et al., Botanical treatment and prevention of malaria, Alternative and Complimentary Therapies, 2004, pp. 277-284, vol. 10, No. 6.

Wright, et al, Natural products and the development of selective antiprotozoal drugs, Phytotherapy Research, 1990, pp. 127-139, vol. 4, No. 4, 3 pages, abstract.

Rosen, International Search Report for PCT/US12/61936, filed Oct. 25, 2012, mailed on Mar. 27, 2013, 17 pages.

Panda, Herbs cultivation and medicinal uses, National Institute of Industrial Re., 2000, 2nd Edition, 6 pages.

Nosten, et al., Artemisinin-based combination treatment of falciparum malaria, Am. J. Trop. Med. Hyg., 2007, pp. 181-192, vol. 77.

Majori, Combined antimalarial therapy using artemisinin, PArassitoligia, 2004, pp. 85-87, vol. 46, Nos. 1-2, 2 pages, abstract.

NutriCology, Innovative Nutrition, Leaders in Innovation and Purity, 2011-2012 Product Catalog, May 15, 2011, 116 pages.

Ferreira, J., et al., Flavonoids from Artemisia annua L. as Antioxidants and Their Potential Synergism with Artemisinin against Malaria and Cancer, Molecules, 2010, pp. 3135-3170, No. 15.

Rosen, et al., European Search Report for European Patent Application No. 12844536.8 filed May 12, 2014 dated Dec. 23, 2014, 8 pages.

Ansel, et al., Pharmaceutical Dosage Forms and Drug Delivery Systems, 1999, 7th edition, pp. 48, 50-53 and 89-91.

Kunimoto, et al., First Case of (Imported) Babesiosis Diagnosed in Canada, Can J Infect Dis, 1998, pp. 387-389, vol. 9, No. 6.

Centers for Disease Control and Prevention, Chikungunya Virus, retrieved Nov. 3, 2015, http://www.cdc.gov/chikungunya/, 3 pages.

WHO, Chikungunya, retrieved Nov. 3, 2015, http://www.who.int/mediacentre/factsheets/fs327/en/, 5 pages.

Akahata, et al., A virus-like particle vaccine for epidemic Chikungunya virus protects nonhuman primates against infection, Nature Medicine, 2010, http://www.nature.com/nm/journal/v16/n3/full/nm.2015.html, 4 pages.

National Institutes of Health, MedlinePlus, Chikungunya virus, retrieved on Nov. 3, 2015, https://www.nlm.nih.gov/medlineplus/ency/patientinstructions/000821.htm, 4 pages.

Shamburger, First human case of Chikungunya virus confirmed in Plano, The Sallas Morning News, Aug. 12, 2015, http://www.dallasnews.com/news/community-news/plano/headlines/20150812-plano-announces-first-human-case-of-chickungunya-virus.ece, 4 pages.

More than 300 cases of Chikungunya Virus in 16 states, Aug. 5, 2015, http://www.theyucatantimes.com/2015/08/more-than-3000-cases-of-chikungunya-virus-in-16-states/, 3 pages.

France-Presse, Spain detects first ever case of mosquito-borne chikungunya virus, Aug. 25, 2015, http://www.theguardian.com/world/2015/aug/26/spain-detects-first-ever-case-of-mosquito-borne-chikungunya-virus, 1 page.

Texas Department of State Health Services, Chikungunya Virus, retrieved on Nov. 3, 2015, http://www.dshs.state.tx.us/idcu/disease/arboviralichikv/, 1 page.

Harding, Mosquito virus dear hits Britons' Caribbean holidays: Tourists warned of deadly disease sweeping islands as thousands return home with agonising symptoms, Daily Mail, Nov. 14, 2014, http://www.dailymail.co.uk/travel/travel_news/article-2834622/Britons-holidaying-Caribbean-warned-deadly-virus-sweeping-islands-37-return-UK-suffering-agonising-symptoms.html, 11 pages.

Pan American Health Organization, World Health Organization, Chikungunya, retrieved on Nov. 4, 2015, http://www.paho/org/hq/?Itemid=40931, 1 page.

Chandak, et al., Neurological complications of Chikungunya virus infection, Nuerological Society of India, 2009, pp. 177-180, vol. 57, issue 2, abstract.

Staples, et al., Chikungunya FeverL an Epidemiological Review of a Re-Emerging Infectious Disease, Clin Infect Dis., 2009, pp. 942-947, vol. 49, No. 6, abstract.

Cotter, First ever Chikungunya virus case pops up in York City, York Dispatch, Jun. 1, 2015, http://www.yorkdispatch.com/breaking/ci_28231567/first-ever-chikungunya-virus-case-pops-up-york, 2 pages.

Carpha's Interim Guidelines, Chikuyngunya Guidelines for Cruise Ships Coming to the Caribbean, Nov. 12, 2014, http://carpha.org/What-We-Do/Public-Health-Activities/Chikungunya, 3 pages.

Urquhart, What Scares Bug Experts? The horrible disease that experts feared would come to the United States has come to the United States, Jul. 2014, http://www.slate.com/articles/health_and_science/medical_examiner/2014/07/chikungunya_virus_in_the_united_states_cdc_and_other_experts_worried_about.html, 2 pages.

1. Based only on how you feel TODAY, in general how would you rate your health and overall quality of life?

2. TODAY, how easy is it for you to bend, kneel, or stoop?

3. TODAY, how easy is it for you to do everyday activities like pushing a vacuum cleaner, doing laundry, shopping for groceries, or walking a moderate distance?

7. TODAY, how would you rate your intake of fluids?

8. TODAY, how would you rate your ability to move and turn your neck?

9. TODAY, how would you rate your ability to sit upright while doing activities: eating, reading, watching TV, being on a computer, or having a conversation?

10. TODAY, how would you rate your sensitivity to light?

11. TODAY, how would you rate your sensitivity to sound?

12. TODAY, how would you rate your overall level of joint pain?

ADDITIONAL ARTEMISININ AND BERBERINE COMPOSITIONS AND METHODS OF MAKING

CROSS REFERENCE TO RELATED APPLICATIONS

The application is a Continuation-In-Part of U.S. patent application Ser. No. 14/614,946 filed Feb. 5, 2015, now U.S. Pat. No. 9,186,331, which is a Divisional patent application of U.S. patent application Ser. No. 13/660,553 filed Oct. 25, 2012, now U.S. Pat. No. 9,011,892, which claims the benefit of priority to U.S. Provisional Patent Application Ser. No. 61/550,969 filed Oct. 25, 2012. The entire disclosure of each of the applications listed in this paragraph are incorporated herein by specific reference thereto.

FIELD OF INVENTION

The present invention relates generally to novel therapeutic compositions, and more specifically to natural botanical ingredients and compositions and methods of making and combining artemisinin, berberine, capsaicin, and papaya extract to produce an Alternative ACT that delivers active therapeutic treatment and prevention of diseases and infections caused by bacteria, viruses and parasites, and more specifically for the treatment of chikungunya.

BACKGROUND AND PRIOR ART

There is renewed and continuing focus on treatments for infections and diseases that include, but are not limited to, malaria, yellow fever, dengue fever, caused by mosquito bites; dysentery caused by bacteria and parasites; Lyme disease and babesiosis, caused by ticks. Often there is not a satisfactory prophylaxis treatment or, in the case of malaria, antimalarial treatments with quinine and other synthetic drugs have resulted in drug resistant strains of malaria which can result in severe adverse outcomes, such as increased mortality, morbidity and medical care costs for patients suffering from common infections, once treatable.

Malaria has four types that can infect humans. Of the four types of malaria, the most life-threatening type is *Plasmodium falciparum*, known to be the most lethal form of the *plasmodium* parasite, causing the greatest number of malaria infections and deaths. Often called jungle fever or swamp fever, malaria is characterized by cycles of chills, fever, and sweating, caused by the parasitic infection of red blood cells by the protozoan parasite *Plasmodium* which is transmitted by the bite of an infected vector for human malarial parasite, a female *Anopheles* mosquito.

The other three types of malaria which include vivax, malariae, and ovale, are generally less serious and are not life-threatening but need to be treated, as their untreated progress can cause a host of health problems.

To date, there is no absolute cure for malaria. Early diagnosis can lead to alleviation of malaria, and prevention remains more effective than treatment. Anti-malarial medication can and should be taken preventively by native populations and travelers in affected regions, such as the tropics and sub-Saharan Africa.

Anti-malarial drugs are available that treat malaria effectively, but there remains the problem of incorrect dosages by self-administering patients, inaccurate combining of ACTs (artemisinin combination therapy) which leads to potential mono-therapeutic treatment with artemisinin and results in highly-resistant strains of malaria, and the lack of adequate delivery systems for children, all of which causes the pattern of repetitive disease to continue.

Another problem is that many of the current ACTs contain some form of quinine, which has long been determined to have serious side effects, especially in children.

Yellow fever is a viral infection and is carried by female mosquitoes of two species (*Aedes* and *Haemogogus*). The "yellow" in the name refers to the jaundice that affects some patients. Mosquitoes pass yellow fever to humans through a small amount of saliva when they bite. The species of mosquito that carry yellow fever are native to sub-Saharan Africa and South America.

Yellow fever can cause flu-like symptoms, fever, headache, muscle pain, chills, nausea, vomiting, yellowing of both the skin and the whites of the eyes, and can cause death. Vaccination is the best way to prevent yellow fever. However, people with compromised immune systems, elderly individuals, and women who may be pregnant or nursing should not receive the vaccine.

There is presently no specific treatment for yellow fever, only supportive care to treat dehydration and fever. Associated bacterial infections can be treated with antibiotics. Supportive care may improve outcomes for seriously ill patients, but it is rarely available in poorer areas.

Prompt detection of yellow fever and rapid response through emergency vaccination campaigns are essential for controlling outbreaks. However, underreporting is a concern and the true number of cases is estimated to be 10 to 250 times what is now being reported. The World Health Organization (WHO) recommends that every at-risk country have at least one national laboratory where basic yellow fever blood tests can be performed. Due to the severe threat of epidemic, and the resultant loss of life on a large scale, one confirmed case of yellow fever in an unvaccinated population should be considered an outbreak, and a confirmed case in any context must be fully investigated, particularly in any area where most of the population has been vaccinated.

Dengue fever is a viral infection transmitted by the bite of an infected mosquito. Mosquitoes can pick up the dengue virus then carry the virus in their own blood, and spread it when they bite humans. The Center for Disease Control and Prevention reports that with more than one-third of the world's population living in areas at risk for transmission, dengue infection is a leading cause of illness and death in the tropics and subtropics. As many as 100 million people are infected yearly. The symptoms of dengue fever resemble symptoms of influenza (flu) and can include fever, severe headache, severe pain behind the eyes, joint pain, muscle and/or bone pain, rash and the like. See for example, Dengue Page, CDC Centers for Disease Control and Prevention, CDC 24/7: http://www.cdc.gov/dengue, Sep. 27, 2012.

Dengue hemorrhagic fever (DHR) is characterized by a fever that lasts from 2 to 7 days, with general signs and symptoms consistent with dengue fever. When the fever declines, hemorrhagic manifestations and low platelet count accompanies other symptoms. There is no specific medication for treatment of a dengue infection. Analgesics, such as acetaminophen, are recommended for pain relief. Aspirin and aspirin-containing drugs should not be taken because aspirin would increase the risk for severe bleeding and hemorrhage.

Dysentery is an intestinal inflammation, especially in the colon, that can lead to severe diarrhea with mucus or blood in the feces. There are two main types of dysentery. Bacillary dysentery is caused by *Shigella*, a bacterium that secretes substances known as cytotoxins, which kill and damage intestinal tissue on contact. Amoebic dysentery (amoebiasis) is caused by *Entamoeba histolytica*, a type of amoeba that reaches the large intestine after entering orally, through ingestion of contaminated food or water, or oral contact with contaminated objects or hands.

Other symptoms that accompany frequent watery stools include abdominal pain, fever and chills, nausea and vomiting. Treatment can include rehydration therapy, administration of antibiotics and amoebicidal drugs. Prevention can include good hygiene, taking measures to reduce risk of infection by regularly washing hands after going to the toilet and before preparing or eating food, drinking water from reliable sources and using purified water to clean your teeth.

Lyme disease is a bacterial infection transmitted by a tick. Lyme disease was first recognized around 1975, after an unusually large number of children were being diagnosed with juvenile rheumatoid arthritis in Lyme, Conn. (USA) and two neighboring towns. Tiny deer ticks infected with the bacterium *Borrelia burgdorferi*, were found to be responsible for the outbreak of arthritis in Lyme.

Not every bite from a deer tick causes Lyme disease. It is more likely to occur if the tick stays attached to an individual's skin for 36 hours or more. Cases have been reported in nearly all states, and the disease is also on the rise in large areas of Asia and Europe.

Lyme disease can be transmitted through a bite from ticks infected with *Borrelia burgdorferi*. In the early stages of Lyme disease, there are flu-like symptoms that can include a stiff neck, chills, fever, swollen lymph nodes, headaches, fatigue, muscle aches and joint pain. There may also be a large, expanding skin rash around the area of the tick bite. Treatment includes antibiotics, such as doxycycline or amoxicillin. The sooner such therapy is begun following infection, the quicker and more complete the recovery. Prolonged antibiotic use may have serious side effects.

In the late stage of the disease, in addition to causing arthritis, Lyme disease can also cause heart, brain and nerve problems.

Babesiosis is a malaria-like illness caused by a protozoan parasite (*Babesia microti* in the United States and other members of the *Babesia* genus in Europe) that invades red blood cells, and is primarily transmitted by the deer tick *Ixodes scapularis* and possibly other related Ixodid ticks.

In Europe, reported fatal cases of babesiosis have occurred mostly in patients whose spleens have been removed, rendering them more vulnerable to infection. The offending parasites in these cases have been either *B. divergens* or *B. major*, to which humans (with spleens intact) are thought to be naturally resistant. In the U.S., reported fatal cases have occurred in patients both with and without spleens; *B. microti* may be a more virulent agent to which humans are not naturally resistant. However, while many in the U.S. who are exposed to the parasite do suffer severe symptoms, fatalities generally occur in elderly patients with compromised immune systems. The heightened risk is in misdiagnosis; since the illness presents like a severe case of influenza, many of those infected do not seek treatment. Unlike Lyme disease, babesiosis does not always present with a tell-tale rash, making it more difficult to suspect. There is a 20% mortality rate for those who are severely infected and do not receive treatment.

Babesiosis cases have been on the rise in the U.S. since the first human case was recognized on Nantucket Island (off the coast of Massachusetts) in 1968. Due to climate changes, the expanding domain of ticks that carry the parasite, and greater human and pet interaction with areas containing the ticks, babesiosis now presents a real danger to those residing and venturing into areas of contamination. The deer (black-legged) tick in the Northeast and upper Midwest, and the Western black-legged tick on the Pacific coast are the primary carriers. A majority of reported cases occur during the summer months along the immediate coast and off-shore islands of the Northeast, but the ticks have now migrated to areas of the Mid-Atlantic and further South.

The symptoms of babesiosis normally begin about a week after a tick bite with a gradual onset of malaise, anorexia and fatigue. This is followed several days later by high fever, drenching sweats, muscle pain and headaches. As with malaria, these symptoms can continue over a protracted period or can abate, then recur. Diagnosis can involve examining blood smears and recognizing the characteristic "ring" form taken by the *Babesia* parasite within the red blood cells of the patient. Recommended treatment has included a seven-day course of oral quinine plus clindamycin under the careful supervision of a physician. Both of these remedies have been used on malaria as well, now to be supplanted by the more preferable ACTs. Since quinine has known negative side effects, and can be harmful to both children and pregnant women, a natural ACT with no known side effects should be the preferred course of treatment. Without it, fatigue, malaise and a low grade fever may persist for weeks or months after quinine and clindamycin treatment has been completed.

Progressive multifocal leukoencephalopathy (PML) is a disease of the white matter of the brain, caused by a virus infection that targets cells that make myelin (the material that insulates neurons). PML is a demyelinating disease, in which the myelin sheath covering the axons of nerve cells is gradually destroyed, impairing the transmission of nerve impulses. It affects the subcortical white matter, particularly that of the parietal and occipital lobes. PML is similar to another demyelinating disease, multiple sclerosis, but progresses much more quickly.

A certain strain of polyomavirus (referred to as John-Cunningham Virus, JCV) is carried by a majority of people and is harmless except among those with lowered immune defenses. It seems that by lowering the immune reaction, the JCV virus is reactivated and is causing demyelinization leading to PML. The PML disease is rare and occurs in patients undergoing chronic corticosteroid or immunosuppressive therapy for organ transplant, or individuals with cancer (such as Hodgkin's disease or lymphoma). Individuals with autoimmune conditions such as multiple sclerosis, rheumatoid arthritis, and systemic lupus erythematosis (some of whom are treated with biological therapies that allow JCV reactivation) are at risk for PML as well.

PML is most common among individuals with human immunodeficiency virus (HIV-1) infection; as well as acquired immune deficiency syndrome (AIDS). Studies estimate that prior to effective antiretroviral therapy, as many as 5 percent of persons infected with HIV-1 eventually develop PML that is an AIDS-defining illness. However, current HIV therapy using antiretroviral drugs (ART), which effectively restores immune system function, allows as many as half of all HIV-PML patients to survive, although they may sometimes have an inflammatory reaction in the regions of the brain affected by PML A diagnosis of PML can be made following brain biopsy or by combining observations of a progressive course of the disease, consistent white matter lesions visible on a magnetic resonance imaging (MRI) scan, and the detection of the JCV in spinal fluid.

Symptoms can include weakness or paralysis, vision loss, impaired speech, and cognitive deterioration, the most prominent symptoms can include clumsiness; progressive weakness; and visual, speech, and personality changes. In addition, the lesions affecting the parietal and occipital lobes can lead to a phenomenon known as alien hand syndrome. The symptoms of PML are diverse, since they are related to the location and amount of damage in the brain, and may evolve over the course of several weeks to months. The progression of deficits leads to life-threatening disability and (frequently) death.

PML can be diagnosed by testing for JCV DNA (deoxyribonucleic acid) in cerebrospinal fluid or in a brain biopsy specimen. Characteristic evidence of the damage caused by PML in the brain can also be detected on magnetic resonance imaging (MRI) images, which classically show multifocal nonenhancing lesions without mass effect. The most common area of involvement is the cortical white matter, but the brainstem and cerebellum may also be involved.

There is no known cure for PML. In some cases, the disease slows or stops if the patient's immune system improves; some AIDS patients with PML have been able to survive for several years, with the advent of highly active antiretroviral therapy (HAART). AIDS patients who start HAART after being diagnosed with PML tend to have a slightly longer survival time than patients who were already on HAART and then develop PML. A rare complication of effective HAART is immune reconstitution inflammatory syndrome (IRIS), in which increased immune system activity actually increases the damage caused by the infection; although IRIS is often manageable with other types of drugs, it is extremely dangerous if it occurs in PML.

Other antiviral agents that have been studied as possible treatments for PML include cidofovir and interleukin-2, but this research is still preliminary. Cytarabine (also known as ARA-C), a chemotherapy drug used to treat certain cancers, has been prescribed on an experimental basis for a small number of non-AIDS PML patients. It is reported to have stabilized the neurological condition of a minority of these patients. One patient regained some cognitive function lost as a result of PML.

In June 2010, the first case report appeared of a PML patient being successfully treated with mefloquine. Mefloquine is an antimalarial drug that can also act against the JCV. Administration of mefloquine seemed to eliminate the virus from the patient's body and prevented further neurological deterioration. It is our thought and hope, that with a study conducted by the H. Lee Moffitt Cancer Center & Research Institute in Tampa Fla. using our ACT, which is devoid of the potentially damaging quinine and its derivatives, but is similar in action to mefloquine against malaria, may eventually prove to be an effective agent against the JCV, and subsequently lead to the successful safe treatment of PML patients. See for example, T E Gofton, A Al-Khotani, B O'Farrell, et al. Mefloquine in the treatment of progressive multifocal leukoencephalopathy. *Journal Neurolology and Neurosurgery Psychiatry* (2010). 82(4):452-5

*Helicobacter pylori* (HP) was first discovered in the stomachs of patients with gastritis and stomach ulcers by Dr Barry J. Marshall and Dr J. Robin Warren, both of Australia. In 1982, conventional thinking held that bacteria could not live in the human stomach, due to the high levels of acid present there, similar in strength to the acid found in an auto battery. Marshall and Warren altered the course of medicine with their discovery and for that, were awarded the 2005 Nobel Prize for Medicine and Physiology.

HP is a corkscrew-shaped, Gram-negative bacterium which is present in the stomach lining of approximately 3 billion people worldwide, and is the most common bacterial infection found in humans. Many of those carrying the bacterium have few or no symptoms, with the exception of inflammation of the stomach lining, a condition which is called "gastritis." Gastritis is the underlying condition which can eventually cause ulcers and other digestive ailments. An HP infection maintained for 20-30 years can lead to cancer of the stomach. For this reason, the World Health Organization's International Agency for Research into Cancer has classified HP as a "Class I Carcinogen," likening its danger to the digestive system to that of cigarette smoking to the lungs and respiratory tract.

The diseases are associated with HP can include duodenal ulcers, gastric (stomach) ulcers, stomach cancer, and non-ulcer dyspepsia. Diagnostic testing for HP can include breath tests, blood tests, endoscopies, and biopsies. Common treatment for HP can be heavy dosing of antibiotics, given in combinations of two to four substances, commonly through a Proton Pump Inhibitor. The treatment can be expensive, debilitating, and unsuccessful. Since HP has developed resistance to many commonly used antibiotics, new treatments must be sought out and identified.

Artemisinin Combination Therapy (ACT) has been an alternative treatment which shows great promise in its ability to act as a broad-based antibiotic and anti-parasitic, especially when dealing with infections that are rising through contamination by fecal matter, as HP is known to be. ACTs are less debilitating for the patient, and have no known side effects as many of the currently prescribed antibiotics have. See for example, Goswami S, B. R. (Epub 2012 Jun. 11). Anti-*Helicobacter pylori* potential of artemisinin and its derivatives. *Antimicrobial Agents and Chemotherapy.*, 56(9):4594-607.

Colitis is a disease caused by inflammation of the large intestine, leading to symptoms which can include frequent diarrhea. Diarrheal diseases are among the leading causes of morbidity and mortality in children worldwide, causing 1 billion episodes of illness and 3-5 million deaths annually. In the United States, approximately 20-35 million episodes of diarrhea occur each year in the 16.5 million children who are younger than 5 years, resulting in 300-400 deaths.

Inflammatory bowel disease (IBD) is a generic term used to describe idiopathic disorders that are associated with gastrointestinal (GI) inflammation which can include Crohn's disease (CD), Ulcerative colitis (UC), and Indeterminate colitis. Colitis can have many different causes, which can include infections, including those caused by a virus, parasite, and food poisoning due to bacteria, inflammatory disorders (ulcerative colitis and Crohn's disease), lack of blood flow (including ischemic colitis and HSP), past radiation to the large intestine, Necrotizing enterocolitis (NEC), Allergic colitis, Pseudomembranous colitis, and Colitis secondary to immune deficiency disorder. IBD symptoms can include abdominal pain and bloating that is intermittent and unpredictable, bloody stools, chills, constant urge to have a bowel movement, dehydration, frequent diarrhea, and persistent fever.

The onset of IBD commonly can occur during adolescence and young adulthood. The risk of IBD in family members of an affected individual is approximately 7-22%; a child's risk of acquiring the disease is up to 60%, and this risk is higher if both parents have the disease. The prevalence of UC in the United States is 100-200 per 100,000 population. The incidence of CD is approximately 3-4 per 100,000 population, and the prevalence is approximately 30-100 per 100,000 population.

NEC is a disease of newborns, with low- and very low-birth-weight preterm infants being particularly susceptible. NEC affects approximately 1-5% of patients admitted to neonatal intensive care units (ICUs) and may occur in approximately 2-5% of infants with birth weights lower than 1500 g (approximately 3 lbs. 5 oz.). Allergic colitis is the most common form of colitis during the first year of life.

IBD is generally diagnosed in children aged 5-16 years. It has a bimodal distribution, with an early onset at age 15-25 years and a second smaller peak at age 50-80 years. The prevalence of IBD is increased among Jewish people of European Ashkenazi descent. A positive family history is the most consistent risk factor for children with IBD. HSP is common in Caucasians. Food-allergic colitis is believed to be present in approximately 0.5% of all infants.

Complications of IBD can include bleeding from the bowels, perforation in the colon, toxic mega colon, and ulceration of the colon. The most serious acute complication of UC is toxic mega colon with the risk of perforation. The risk of colon cancer increases after 8-10 years of having UC. The complications of CD tend to increase with time and include bowel strictures, fistulas, abscess, and intestinal obstruction. After surgery, patients may develop short bowel syndrome and mal-absorption.

References to colitis can include:

Lee I A, H. Y. (2010). Berberine ameliorates TNBS-induced colitis by inhibiting lipid peroxidation, enterobacterial growth and NF-κB activation. *European Journal of Pharmacology*, 648(1-3):162-70;

Zhang M, L. Y. (2011). Evidence for the complementary and synergistic effects of the three-alkaloid combination regimen containing berberine, hypaconitine and skimmianine on the ulcerative colitis rats induced by trinitrobenzenesulfonic acid. *European Journal of Pharmacology*, 651(1-3): 187-96;

Yan F, W. L. (2012). Berberine promotes recovery of colitis and inhibits inflammatory responses in colonic macrophages and epithelial cells in DSS-treated mice. *American journal of physiology. Gastrointestinal and liver physiology*, 302(5):G504-14;

Li G H, W. D. (2012). Berberine inhibits acute radiation intestinal syndrome in human with abdomen radiotherapy. *Medical Oncology*, 27(3):919-25; and Kawashima K, N. A. (2004). Pharmacological properties of traditional medicine (XXIX): effect of Hange-shashin-to and the combinations of its herbal constituents on rat experimental colitis. *Biological and pharmaceutical bulletin*, 1599-603.

Natural substances, such as artemisinin, as well as derivatives and modifications thereof, have been used for many years as natural medications for treating infections and diseases caused by bacteria, viruses and parasites.

According to N. J. White in "Assessment of the pharmacodynamic properties of antimalarial drugs in vivo" *Antimicrobial. Agents Chemotherapy*. 41 (7): 1413-1422 (July 1997), artemisinin, and its derivatives are a group of herbal compounds that possess the most rapid action of all current drugs against *falciparum* malaria. Treatments containing an artemisinin derivative (artemisinin-combination therapies, ACTs) are now standard treatment worldwide for *falciparum* malaria. The starting compound artemisinin is isolated from the plant *Artemisia annua*, an herb described in Chinese traditional medicine.

For many years after the discovery, access to the purified drug and the plant it was extracted from were restricted by the Chinese government. It was not until the later 1970s and early 80s that news of the discovery reached scientists outside China. In 2006, after artemisinin had become the treatment of choice for malaria, the World Health Organization (WHO) called for an immediate halt to single-drug artemisinin preparations in favor of medications that combine artemisinin with another malaria drug, in order to reduce the risk of parasites developing resistance, as reported in a WHO Media Center News Release dated 19 Jan. 2006. Thus the use of artemisinin by itself as a monotherapy is explicitly discouraged by the World Health Organization because there are signs that malarial parasites are developing resistance to artemisinin alone.

Following is a list of patents that focus on the chemistry of artemisinin and its derivatives which include artesunate, dihydroArtemisinin and derivatives thereof used in antimalarials, mixed steroidal compounds, trioxane derivatives, and the like. U.S. Pat. No. 7,098,242 to ElSohly et al.; U.S. Pat. No. 7,071,226 to Singh et al.; U.S. Pat. No. 6,984,640 to Haynes et al.; U.S. Pat. No. 6,906,205 to Vennerstrom et al.; U.S. Pat. No. 6,906,098 to Solaja et al.; U.S. Pat. No. 6,750,356 to Bhakuni et al.; U.S. Pat. No. 6,737,438 to Singh et al.; U.S. Pat. No. 6,685,972 to Kumar et al.; U.S. Pat. No. 6,683,193 to Bhakuni et al.; U.S. Pat. No. 6,649,647 to Haynes et al.; U.S. RE38,117 to Zheng et al.; U.S. Pat. No. 6,461,603 to Bentley et al.; U.S. Pat. No. 6,346,631 to Jain et al.; U.S. Pat. No. 6,306,896 to Scheiwe; U.S. Pat. No. 6,160,004 to Posner et al.; U.S. Pat. No. 6,136,847 to Posner et al.; U.S. Pat. No. 6,127,405 to Kumar et al.; U.S. Pat. No. 5,856,351 to Zheng et al.; U.S. Pat. No. 5,225,562 to McChesney et al.; and U.S. Pat. No. 5,225,427 to Venugopalan et al.

U.S. patents covering various uses of berberine and derivatives thereof include U.S. Pat. Nos. 5,153,178; 4,980,344; 4,749,708; and 4,761,417 to Maroko.

Various patents provide the state of the art for synthetic drugs combined with natural herbal compounds, such as, artemisinin and berberine; the combination includes chemical and natural ingredients. A representative sample of patents and patent publications is provided below.

U.S. Pat. No. 8,026,209 to Gaillard et al. identifies antimalarials, such as artemisinin and berberine in the production of pharmaceutical compositions for targeting agents into and across the blood-barrier and other endothelial cell microvascular barriers.

U.S. Pat. No. 7,947,846 to Frincke discloses use of synthesized compounds to treat thrombocytopenia, neutropenia or delayed effects of radiation therapy and mentions that optional administration of additional therapeutic treatments could include analogs for viral infections or antimalarial agents such as artemisinin and berberine.

U.S. Pat. No. 7,935,839 to Frincke discloses sepsis treatment methods for cystic fibrosis, neutropenia that could include optionally administered additional therapeutic treatment from antimalarials, such as artemisinin and berberine.

U.S. Pat. No. 7,915,223 to Mor et al. discloses a novel class of antimicrobial polymeric agents and pharmaceutical compositions containing the same for treating medical conditions associated with pathological microorganisms and more. Mor et al. mentions artemisinin in combination with other drugs is preferred treatment for resistant strains of malaria.

U.S. Pat. No. 7,547,687 to Reading et al. discloses compounds used for treatment of cystic fibrosis, neutropenia that could include optionally administered additional therapeutic treatment from antimalarials, such as artemisinin and berberine.

U.S. Pat. No. 7,482,334 to Frincke et al. mentions therapeutic treatment methods using synthetic compounds and natural substances to ameliorate or treat cystic fibrosis, neutropenia and other conditions.

U.S. Pat. No. 5,413,928 to Weathers et al. references plants grown in vitro can provide a major source of specialty chemicals, which are plant secondary metabolites, such as artemisinin, a terpenoid found in the herb, *Artemisia annua*, to provide therapeutic treatment for malaria. Weathers et al. also reference that berberine, an alkaloid compound, can be extracted from the roots, rhizomes, stems and bark of a variety of *Berberis* plants, such as Oregon grape, Barberry, Tree Turmeric, Goldenseal, and others.

ActRx at website http.//actrxlimited.com/ (n.d.). retrieved October 2012 from ActRx: www.actrxlimited.com offers for sale a malaria-Dengue formular stating that all ingredients are rated GRAS (Generally Recognized As Safe); the ActRx adult formula has packet A, serving size two tables; artesnunate 50 mg and packet B Berberine alkaloid, service size two tablets 800 mg; and ActRx 80 mg injectable for malaria (no formula given). The product is packaged and offered in a manner that could lead to a consumer taking packet A and not packet B or vice versa and otherwise resulting in ineffective remediation of the disease or infection.

Thus, the prior art suggests that many chemical and natural compounds can be combined to provide therapeutic treatment for diseases, such as malaria. What is absent in the prior art is a formulation that combines, in one unit, such as a pill or tablet, two all-natural, herbal substances, namely, artemisinin and berberine, to deliver active therapeutic substances to relieve suffering from devastating infectious diseases, including, but not limited to malaria, yellow fever, dengue fever, dysentery, Lyme disease, babesiosis, progressive multifocal leukoencephalopathy, *Helicobacter Pylori*, and colitis.

There is also an obvious need for an ACT with a more effective and passively accurate delivery system, devoid of quinine, with all natural active ingredients, and in a form accessible and agreeable to children. The present invention fulfills this need as a treatment and as a preventive agent.

SUMMARY OF THE INVENTION

The first objective of the present invention is to provide a composition of all-natural herbal ingredients for adults combining artemisinin and berberine formulated to deliver in one single unit or pill a therapeutically effective treatment for malaria, dengue fever, dysentery, yellow fever, Lyme disease, babesiosis, progressive multifocal leukoencephalopathy, *Helicobacter Pylori*, and colitis.

The second objective of the present invention is to provide a composition of all-natural herbal ingredients for children combining artemisinin and berberine formulated to deliver in one single unit or pill a therapeutically effective treatment for malaria, dengue fever, dysentery, yellow fever, Lyme disease, babesiosis, progressive multifocal leukoencephalopathy, *Helicobacter Pylori*, and colitis.

The third objective of the present invention is to provide a composition of all-natural herbal ingredients for adults combining artemisinin and berberine formulated to deliver a single pill for the prevention of malaria, dengue fever, dysentery, yellow fever, Lyme disease, babesiosis, progressive multifocal leukoencephalopathy, *Helicobacter Pylori*, and colitis.

The fourth objective of the present invention is to provide a composition of all-natural herbal ingredients for children combining artemisinin and berberine formulated to deliver a chewable tablet or dosing system for prevention of malaria, dengue fever, dysentery, yellow fever, Lyme disease, babesiosis, progressive multifocal leukoencephalopathy, *Helicobacter Pylori*, and colitis.

The fifth objective of the present invention is to provide a composition of all-natural herbal ingredients combining artemisinin and berberine for treatment and prevention of chloroquine-resistant and anti-malarial drug-resistant strains of malaria in humans or animals.

The sixth objective of the present invention is to provide a composition of all-natural herbal ingredients combining artemisinin and berberine that is devoid of quinine or quinine derivatives for treatment and prevention malaria, dengue fever, dysentery, yellow fever, Lyme disease, babesiosis, progressive multifocal leukoencephalopathy, *Helicobacter Pylori*, and colitis, in humans or animals.

The seventh objective of the present invention is to provide a composition of all-natural herbal ingredients combining artemisinin and berberine in a single pill, tablet, capsule, or delivery system that functions as a passively accurate dosing and delivery system for treatment and prevention of malaria, dengue fever, dysentery, yellow fever, Lyme disease, babesiosis, progressive multifocal leukoencephalopathy, *Helicobacter Pylori*, and colitis, in humans or animals.

An eighth objective of the invention is to provide natural botanical ingredients and compositions and methods of making and combining artemisinin, berberine, capsaicin, and papaya extract to produce an Alternative ACT that delivers active therapeutic treatment and prevention of diseases and infections caused by bacteria, viruses and parasites, and more specifically for the treatment of chikungunya.

An artemisinin and berberine treatment composition for treating a patient in a single pill, tablet or capsule can include artemisinin, berberine, and at least one binding or delivery component, wherein the composition is useful for treating an adult in a single pill, tablet or capsule, for at least one illness selected from the group comprising malaria, dengue fever, dysentery, yellow fever, Lyme disease and babesiosis, progressive multifocal leukoencephalopathy, *Helicobacter Pylori*, and colitis.

The treatment composition can be used for an adult patient and includes a broad range 50 mg-120 mg artemisinin, and 350 mg-1000 mg berberine. A preferred range can include 90 mg-110 mg artemisinin and 600 mg-900 mg berberine. An example can include approximately 100 mg artemisinin and approximately 800 mg berberine.

For the adult application, the at least one binding or delivery component can be selected from the group comprising: microcrystalline cellulose, stearic acid, silicon dioxide, calcium carbonate, magnesium stearate, and croscarmellose sodium.

The treatment composition can be used for an child patient and include 12.5 mg-30 mg artemisinin and 87.5 mg-250 mg berberine. A preferred range can include 22.5 mg-27.5 mg artemisinin and 150 mg-225 mg berberine. An example can include approximately 25 mg artemisinin and approximately 200 mg berberine.

For the child patient, the at least one binding or delivery component can be selected from the group comprising: peppermint, xylitol, maltodextrin, sucralose, silicon dioxide, calcium carbonate, and precipitated silica.

Another artemisinin and berberine composition for treating a patient in a single pill, tablet or capsule can include the combination of artemisinin. berberine, and a blended mixture of up to approximately 400 mg of black walnut (*Juglans nigra*) dry outer hull and up to approximately 500 mg of wormwood (*Artemisia absinthium*) dry flower and leaf; up to approximately 150 mg of Clove (*Syzygium aronalicum*) dry flower; and up to approximately 700 mg of Chinese wormwood (*Artemisia annua*), wherein the composition is useful for prevention of at least one of malaria, dengue fever, dysentery, yellow fever, Lyme disease, babesiosis, progressive multifocal leukoencephalopathy, *Helicobacter Pylori*, and colitis.

A method for making an artemisinin and berberine composition for a patient in a single pill, tablet, capsule, gelcap, oral suspension, sublingual or transdermal patch, or any other therapeutic preparation can include the steps of providing a mixer, mixing artemisinin and berberine in the mixer to form mixture (I), mixing at least one binding or delivery component with mixture (I) to form mixture (II), filtering mixture (II) through at least one filter to form mixture (III), granulating mixture (III) in a granulator to produce granulated chips, pressing the granulated chips into tablets (mixture IV), removing dust from the tablets by cleaning and vacuuming the tablets, applying an enteric shell coating to the cleaned and vacuumed tablets heating and tumbling the coated tablets, and packaging the heated and tumbled coated tablets in a package.

The method for making an artemisinin and berberine composition can include the steps of selecting 50 mg-120 mg artemisinin and selecting 350 mg-1000 mg berberine.

The method for making an artemisinin and berberine composition can include the steps of selecting the at least one binding or deliver component is selected from the group comprising: microcrystalline cellulose, stearic acid, silicon dioxide, calcium carbonate, magnesium stearate, and croscarmellose sodium.

The method for making an artemisinin and berberine composition can include the steps of selecting 12.5 mg-30 mg artemisinin, and selecting 87.5 mg-250 mg berberine.

The method for making an artemisinin and berberine composition can include the steps of selecting the at least one binding or deliver component is selected from the group comprising: peppermint, xylitol, maltodextrin, sucralose, silicon dioxide, calcium carbonate, and precipitated silica.

A therapeutic treatment composition, can consist only of a mixture of artemisinin and berberine in a single capsule, wherein the composition is adaptable for treatment of mammals, or birds with an infection caused by at least one of a parasite, a bacteria, a virus, and a combination thereof. The infection can be selected from the group comprising malaria, dengue fever, dysentery, yellow fever, Lyme disease and babesiosis, progressive multifocal leukoencephalopathy, *Helicobacter Pylori*, and colitis.

The mixture can include 50 mg-120 mg artemisinin and 350 mg-1000 mg berberine. The mixture can also include 12.5 mg-30 mg artemisinin and 87.5 mg-250 mg berberine.

Natural botanical ingredients and compositions and methods of making and combining artemisinin, berberine, capsaicin, and papaya extract to produce an Alternative ACT that delivers active therapeutic treatment and prevention of diseases and infections caused by bacteria, viruses and parasites, and more specifically for the treatment of chikungunya.

Further objects and advantages of this invention will be apparent from the following detailed description of a presently preferred embodiment, when read in conjunction with the appended claims.

DETAILED DESCRIPTION OF THE PREFERRED EMBODIMENTS

Figure 1:
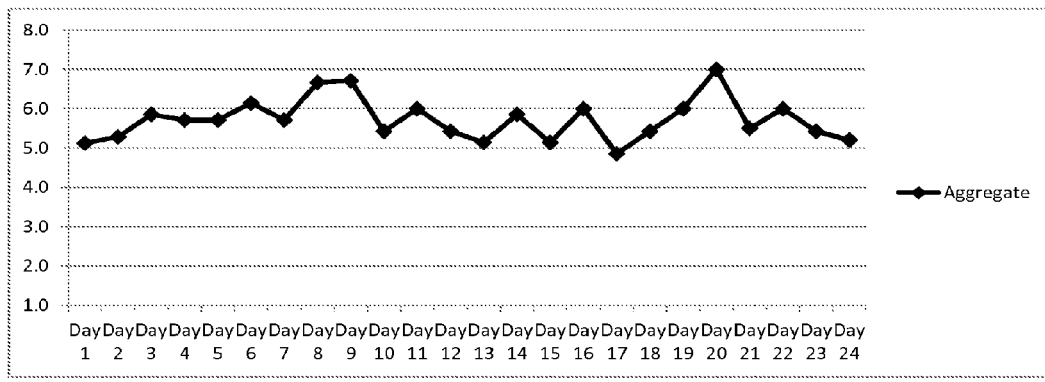
FIG. 1 is a graph of a Lyme focus group survey results for rating quality of life.

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

The delivery system described in this patent includes, but is not limited to, the following methods of packaging: blister packs, zip lock packs, standup pouches, foil pouches, boxes, jars, bottles, single dose packets, one a day packs, two day packs, three day packs, four day packs, five day packs, six day packs, seven day packs, 8, 9, 10, 11, 12 or 13 or more day packs, fourteen day packs, 15, 16, 17, 18, 19, 20, 21, 22, 23, 24, 25, 26, 27, 28, 29 and thirty day packs or more, sixty day packs, ninety day packs, spray bottles, fast melt pill format, bursts, gel format adhesive bandages, skin patches, gelcaps, softgels, gelatin capsules, vegetarian capsules, hard shell gelatin capsules, injections, intravenous solutions, topical creams, topical ointments, suppositories, or sublingual methods of administration known to those versed in the art.

It would be useful to discuss the meanings of some words used herein and their applications before discussing the compositions of matter and method of using as a carrier in a topical skin application.

The acronym ACT is used herein to mean "Artemisinin Combination Therapy" which includes artemisinin and its derivatives in combination with other therapeutic substances.

The compound "crosmellose sodium" is an internally cross-linked sodium carboxy-methylcellulose for use as a disintegrant in pharmaceutical formulations. The cross-linking reduces water solubility while still allowing the material to swell (like a sponge) and absorb many times its weight in water. As a result, it provides superior drug dissolution and disintegration characteristics, thus improving formulas' subsequent bioavailability by bringing the active ingredients into better contact with bodily fluids.

Croscarmellose sodium also resolves formulators' concerns over long-term functional stability, reduced effectiveness at high tablet hardness levels, and similar problems associated with other products developed to enhance drug dissolution. Croscarmellose sodium is a very commonly used pharmaceutical additive approved by the U.S. Food and Drug Administration. Its' purpose in most tablets—including dietary supplements—is to assist the tablet in disintegrating in the intestinal tract at the required location.

The term "dysentery" is used herein to include diarrhea, cholera and traveler's diarrhea. Acute diarrhea is usually related to a bacterial, viral, or parasitic infection. Chronic diarrhea is usually related to functional disorders such as irritable bowel syndrome or inflammatory bowel disease. Cholera is an acute infection in humans involving the entire small bowel, characterized by a debilitating diarrhea. Traveler's diarrhea is the most common illness affecting travelers. The most important determinant of risk is the traveler's destination with the primary source of infection being the ingestion of fecally contaminated food or water. Common culprits causing the disorder include *Campylobacter, Salmonella, Shigella* and *Escherichia coli* (*E. coli*).

The term "excipient" is used herein to mean an inert substance added to a pharmaceutical composition to further facilitate administration of the compound. Excipients can include flavors, sugars, starches, cellulose derivatives, gelatin, calcium carbonate, magnesium stearate, silicon dioxide, masking agents and the like.

The term "preventative" and "prevent" is used herein to mean avoiding and preventing the appearance of clinical symptoms of a condition.

The term "therapeutically effective amount" is used herein to describe an amount of the composition being administered which will relieve to some extent or prevent one or more of the symptoms of the condition being treated.

The term "treating" and "treatment" is used herein to mean abrogating, substantially inhibiting, slowing or reversing the progression of a condition, substantially ameliorating clinical symptoms of a condition.

The present invention comprises all natural active ingredients formulated with various selected excipients to provide the treatments and therapies disclosed herein. This is an advantage over the prior art wherein chemicals and synthetic drugs are used for treatment and prevention. The use of chemicals can cause harmful side effects.

Before discussing the compositions of the present invention and the method for making, a brief discussion is provided of each of the all-natural active ingredients, artemisinin and berberine.

Artemisinin is produced from a plant-based source, the *Artemisia annua*. China and Vietnam provide 70% and East Africa 20% of the raw material. Seedlings are grown in nurseries and then transplanted into fields. It takes about 8 months to reach full size. The plants are harvested, the leaves are dried and sent to facilities where the artemisinin is extracted using solvent, typically hexane. Artemisinin and its derivative forms are commercially available from India or China. One supplier of artemisinin is Tai'an Zhonghui Plant Biochemical Co., Ltd. Taifeng Road, No. 88, Zhaizhen Industry District, Xintai, Shandong, China. Artemisinin and its derivatives have half-lives in the order of a few hours and thus require at least daily dosing for several days.

Berberine is a strongly yellow colored quaternary ammonium salt, known as an alkaloid. It is found in the roots, rhizomes, stems and bark of a variety of plants, including, but not limited to Barberry, Tree Turmeric, Goldenseal, Prickly Poppy, Californian Poppy and the like. In addition to use as a natural dye, berberine is considered an antibiotic and has been included in formulations as a traditional medicine or dietary supplement to treat fungal infections, *Candida albicans*, yeast, parasites, bacterial/viral infections, and eye infections with wide potential therapeutic properties.

Berberine is commercially available. One of many suppliers is Hopeland Chem-Tech Co., Ltd. Rm.2-0103, Gaoke Plaza D, No. 3, 4$^{th}$ Gaoxin Road, Xi'an City, Shaanxi Province, China. Berberine is one of the bitterest substances known. It is also difficult to work within the formation of dry, physically stable pills due to its water content, which is approximately 14 weight %.

Not to be bound by any theory, it is believed that artemisinin destroys the bacteria, virus or parasite in the blood and berberine destroys the weakened, but still viable bacteria, virus or parasite in the intestines. Artemisinin and berberine combined have no known toxicity to humans at the dosage levels required for effective treatment and prevention of infections caused by bacteria, viruses and parasites in humans.

Table IA below provides a list of ingredients that are used to provide a basic formulation of artemisinin and berberine (AB) for treatment of an adult person suffering from malaria, dengue fever, dysentery, yellow fever, Lyme disease or babesiosis. Table 1A is intended to cover an average adult weighing approximately 180 pounds (approximately 81.65 kg).

TABLE IA

Treatment Composition mg per pill for Adult

| Component - Adult Dosing | Broad Range (mg per Pill) | Preferred Range (mg per Pill) | Preferred Amt (mg per Pill) | Substitution Category |
|---|---|---|---|---|
| ACTIVE INGREDIENTS | | | | |
| artemisinin | 50-120 mg | 90-110 mg | approx 100 mg | |
| berberine | 350-1000 mg | 600-900 mg | approx 800 mg | |
| INERT INGREDIENTS | For binding or delivery of other ingredients. | | | |
| microcrystalline cellulose | 0-650 | 400-650 | approx 540 | Binders and compaction |
| stearic acid | 0-200 | 200-400 | approx 300 | Lubricant excipient |
| silicon dioxide | 0-50 | 30-50 | approx 40 | Water reducing agent and promote absorption of water and prevent caking and clumping |
| calcium carbonate | 0-1100 | 800-1100 | approx 1000 | Inert filler |
| magnesium stearate | 0-90 | 60-90 | approx 75 | For lubricating properties and to prevent powdered component from sticking to pill press equipment during compression from powder into solid tablets |
| croscarmellose sodium | 0-50 | 35-50 | approx 40 | To reduce water solubility and allow material to expand, absorbing many times its weight in water and removing much of the water from berberine. |

Approximately is defined as +1-5% in order to cover manufacturing variances and dosing tolerances.

The inert ingredients are not therapeutic and are designed for the integrity, palatability and stability of the tablets. There are many substitutes for the various classes of inert ingredients that can include disintegrants, lubricants, binders, and excipients.

Disintegrants can include, but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

ics, fillers and stearates. dehydrating agents or desiccating agents.

Desiccating agents can include but are not limited to sodium carboxy methyl cellulose, silica gel, microcrystalline cellulose, carboxymethylcellulose calcium, cellulose, colloidal silicone dioxide, and crosscarmellose sodium.

Table IB covers a dose per body weight (in mg per kg) for customizing dosages for adults less than or greater than 180 pounds (81.65 kgs).

TABLE IB

DOSE PER BODY WEIGHT FOR ADULTS (mg per kg)

| Component - Adult Dosing | Broad Range (mg per kg) | Preferred Range (mg per kg) | Preferred Amt ((mg per kg) | Substitution Category |
|---|---|---|---|---|
| ACTIVE INGREDIENTS | | | | |
| artemisinin | 22.69-54.43 | 40.92-49.90 | approx 45.36 | |
| berberine | 158.76-453.60 | 272.15-408.03 | approx 362.87 | |
| INERT INGREDIENTS | For binding or delivery of other ingredients. | | | |
| microcrystalline cellulose | 0-294.83 | 181.99-294.83 | approx 244.94 | Binders and compaction |
| stearic acid | 0-181.44 | 90.72-181.44 | approximately 136.08 | Lubricant excipient |
| silicon dioxide | 0-22.68 | 13.61-22.68 | approx 18.14 | Water reducing agent and to promote absorption of water and prevent caking and clumping |
| calcium carbonate | 0-498.95 | 362.89-498.95 | approx 453.59 | Inert filler |
| magnesium stearate | 0-40.82 | 27.22-40.82 | approx 34.02 | For lubricating properties and to prevent powdered component from sticking to the pill press equipment during the compression from powder into solid tablets |
| croscarmellose sodium | 0-22.68 | 15.88-22.68 | approx 18.14 | To reduce water solubility and allow the material to expand, absorbing many times its weight in water and removing much of the water from Berberine. |

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, povidone.

Excipients can include but are not limited to flavorings, cellulose derivatives, calcium carbonate, magnesium stearate, silicon dioxide, masking agents, saccharides and their derivatives, gelatin, Synthetic polymers, coatings and enter- Approximately is defined as +/−5% in order to cover manufacturing variances and dosing tolerances.

In the tables, a gel cap example can consist of only artemisinin and berberine in the amounts referenced in the above tables.

For adults, defined as persons over the body weight of 110 pounds, one tablet can be one serving size and recommended directions for taking the anti-malarial composition are as follows:
Day 1—Take one tablet in the morning
    Take one tablet in the evening
Day 2—Take one tablet in the morning
    Take one tablet in the evening
Day 3—Take one tablet in the morning
Day 4—Take one tablet in the morning Table II illustrates an Adult Treatment Dosing rate.

TABLE II

| Adult Treatment Dosing | | | | |
|---|---|---|---|---|
| Dosing | Day 1 | Day 2 | Day 3 | Day 4 |
| AM | One Tablet | One Tablet | One Tablet | One Tablet |
| PM | One Tablet | One Tablet | | |

The four-day dosage regimen outlined above in Table II as an anti-malarial treatment requires the consumption of a total of 6 tablets over a consecutive four-day period and is also the dosage regimen used in the treatment of dengue fever, dysentery and yellow fever. The dosage regimen for Lyme disease requires the consumption of eighteen tablets over twenty-four consecutive days as shown in Table III.

TABLE III

| Adult Dosing, Lyme Disease | | | | | | | | |
|---|---|---|---|---|---|---|---|---|
| Phase 1 | Day 1 | Day 2 | Day 3 | Day 4 | Day 5 | Day 6 | Day 7 | Day 8 |
| AM | 1 Tablet | 1 Tablet | 1 Tablet | 1 Tablet | 1 Tablet | 1 Tablet | 1 Tablet | 1 Tablet |
| PM | 1 Tablet | 1 Tablet | | | | | | |
| Phase 2 | Day 9 | Day 10 | Day 11 | Day 12 | Day 13 | Day 14 | Day 15 | Day 16 |
| | No Dose | No Dose | No Dose | No Dose | No Dose | No Dose | No Dose | No Dose |
| Phase 3 | Day 17 | Day 18 | Day 19 | Day 20 | Day 21 | Day 22 | Day 23 | Day 24 |
| AM | 1 Tablet | 1 Tablet | 1 Tablet | 1 Tablet | 1 Tablet | 1 Tablet | 1 Tablet | 1 Tablet |

Table IVA provides the formulation of a chewable tablet for children in mg per pill.
Table IVA covers for children having a weight of 27.2 kg (60 pounds).

TABLE IVA

| Treatment Composition for Children in mg per pill | | | | |
|---|---|---|---|---|
| Children's Dosing [mg/Pill] | Broad Range | Preferred Range | Preferred Amount | Substitution Category |
| ACTIVE INGREDIENTS | | | | |
| artemisinin | 12.5-30 | 22.5-27.5 | approx 25 | |
| berberine | 87.5-250 | 150-225 | approx 200 | |
| INACTIVE INGREDIENTS | For binding or delivery of other ingredients. | | | |
| peppermint | 0-70 | 35-70 | approx 50 | Flavoring |
| xylitol | 0-1,200 | 800-1,200 | approx 1,000 | Sweetener |
| 83% maltodextrin and 17% natural flavors | 0-120 | 80-120 | approx 100 | Masking Agent |
| sucralose | 0-12 | 8-12 | approx 10 | Sweetener |
| INERT INGREDIENTS | | | | For binding or delivery of other ingredients |
| silicon dioxide | 0-220 | 160-220 | approx 200 | Water reducing agent that promotes |
| calcium carbonate | 0-1,200 | 800-1,200 | approx 1,000 | absorption of water and prevents caking or clumping Inert filler |
| precipitated silica | 0-29 | 23-29 | approx 26.66 | Anticaking, free flow agent |

Approximately is defined as +/−5% in order to cover manufacturing variances and dosing tolerances.

In the tables, a gel cap example can consist of only artemisinin and berberine in the amounts referenced in the above tables.

The inert ingredients are not therapeutic and are designed for the integrity, palatability and stability of the tablets. There are many substitutes for the various classes of inert ingredients that can include disintegrants, lubricants, binders, excipients Disintegrants can include guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating Agents or Desiccating Agents can include but are not limited to sodium carboxy methyl cellulose, silica gel, microcrystalline cellulose, carboxymethylcellulose calcium, cellulose, colloidal silicone dioxide and crosscarmellose sodium.

Table IVB covers a dose per body weight (in mg per kg) for customizing dosages for children having weights of less than 100 pounds (45.36 kgs).

TABLE IVB

DOSE PER BODY WEIGHT FOR CHILDREN (mg per kg)

| Children's Dosing | Component | | | |
|---|---|---|---|---|
| | Broad Range mg/kg | Preferred Range mg/kg | Preferred Amount mg/kg | Substitution Category |
| ACTIVE INGREDIENTS | | | | |
| artemisinin | 5.67-13.61 | 10.21-12.47 | approx 11.39 | |
| berberine | 39.69-113.40 | 68.04-102.06 | approx 90.72 | |
| INACTIVE INGREDIENTS | For binding or delivery of other ingredients. | | | |
| peppermint | 0-31.75 | 15.88-31.75 | approx 22.68 | Flavoring |
| xylitol | 0-544.31 | 362.87-544.31 | approx 453.60 | Sweetener |
| 83% maltodextrin & 17% natural flavors | 0-54.43 | 36.29-54.43 | approx 45.36 | Masking Agent |
| sucralose | 0-5.44 | 3.63-5.44 | approx 4.54 | Sweetener |
| INERT INGREDIENTS | | | | For binding or delivery of other ingredients |
| silicon dioxide | 0-99.79 | 72.57-99.79 | approx 90.72 | Water reducing agent that promotes absorption of water and prevents caking or clumping |
| calcium carbonate | 0-544.31 | 362.87-544.31 | approx 453.60 | Inert filler |
| precipitated silical | 0-13.15 | 10.43-13.15 | approx 12.09 | Anticaking, free flow agent |

Approximately is defined as +/−5% in order to cover manufacturing variances and dosing tolerances.

In the tables, a gel cap example can consist of only artemisinin and berberine in the amounts referenced in the above tables.

For children, defined as persons between the ages of 2 and 12 with a body weight below 110 pounds, children's dosage size is two tablets; thereby providing approximately 50 mg artemisinin per dosage. Tablets can be chewed or dissolved in the mouth. Directions for taking the anti-malarial formula are as follows:

Day 1—Take two tablets in the morning
　Take two tablets in the evening
Day 2—Take two tablets in the morning
　Take two tablets in the evening
Day 3—Take two tablets in the morning
Day 4—Take two tablets in the morning The four-day dosage regimen outlined above as an anti-malarial treatment requires the consumption of a total of 12 tablets over a consecutive four-day period and is also the dosage regimen used in the treatment of dengue fever, dysentery and yellow fever.

The dosage regimen for Lyme disease requires the consumption of thirty-six tablets over twenty-four consecutive days is shown in Table V.

TABLE V

| Children's Dosing, Lyme | | | |
|---|---|---|---|
| Phase 1 | Day 1 | Day 2 | Days 3-8 |
| AM | 2 Chewables | 2 Chewables | 2 Chewables |

TABLE V-continued

| Children's Dosing, Lyme | | | |
|---|---|---|---|
| PM | 2 Chewables | 2 Chewables | |
| Phase 2 | Day 9 | Day 10 | Days 11-16 |
| | No Dose | No Dose | No Dose |
| Phase 3 | Day 17 | Day 18 | Days 19-24 |
| AM | 2 Chewables | 2 Chewables | 2 Chewables |

Table VIA shows a table for the preventative composition for adults in mg per pill.

TABLE VIA

Preventative Composition for Adults in mg per pill

| Adult Dosing [mg/Pill] | Component Preventative | | | |
|---|---|---|---|---|
| | Broad Range | Preferred Range | Preferred Amount | Substitution Category |
| ACTIVE INGREDIENTS | | | | |
| artemisinin | 50-120 mg | 90-110 mg | approx 100 mg | |
| berberine | 350-1000 mg | 600-900 mg | approx 800 mg | |
| BLENDED MIXTURE* | 0-500 mg | 300-500 mg | approx 350 mg | Excipient with Active Ingredients |
| INERT INGREDIENTS | | For binding or delivery of other ingredients. | | |
| microcrystalline cellulose | 0-650 | 400-650 | approx 540 | Binders and compaction |
| stearic acid | 0-200 | 200-400 | approx 300 | Lubricant excipient |
| silicon dioxide | 0-50 | 30-50 | approx 40 | Water reducing agent and to promote absorption of water and prevent caking and clumping |
| calcium carbonate | 0-1100 | 800-1100 | approx 1000 | Inert filler |
| magnesium stearate | 0-90 | 60-90 | approx 75 | For lubricating properties and to prevent powdered component from sticking to the pill press equipment during the compression from powder into solid tablets |
| croscarmellose sodium | 0-50 | 35-50 | approx 40 | To reduce water solubility and allow the material to expand, absorbing many times its weight in water and removing much of the water from Berberine. |

Approximately is defined as +/−5% in order to cover manufacturing variances and dosing tolerances.

In the tables, a gel cap example can consist of only artemisinin and berberine in the amounts referenced in the above tables.

The inert ingredients are not therapeutic and are designed for the integrity, palatability and stability of the tablets. There are many substitutes for the various classes of inert ingredients that can include disintegrants, lubricants, binders and excipients.

Disintegrants can include but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating Agents or Desiccating Agents can include but are not limited to sodium carboxy methyl cellulose, silica gel, microcrystalline cellulose, carboxymethylcellulose calcium, cellulose, colloidal silicone dioxide, and crosscarmellose sodium.

*The blended mixture referenced in Table VI can include a blended mixture approximately 400 mg of concentrate of black walnut (*Juglans nigra*) dry outer hull; approximately 500 mg of concentrate of organically grown wormwood (*Artemisia absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

For adults, defined as persons with a body weight of at least 110 pounds, one capsule per day with a meal is taken for 7 to 14 days depending on the number of days desired to stay parasite free. One capsule per day for 7 to 14 days is effective for preventing infection for 30 to 60 days, respectively. A dosage of one capsule a day for 14-28 days is effective for preventing Lyme disease for 30 to 60 days, respectively.

Table VIB covers a dose per body weight (in mg per kg) for customizing dosages for adults less than or greater than 180 pounds (81.65 kgs).

Approximately is defined as +/−5% in order to cover manufacturing variances and dosing tolerances.

In the tables, a gel cap example can consist of only artemisinin and berberine in the amounts referenced in the above tables.

Table VIIA shows the formulation of a chewable tablet for children.

TABLE VIB

DOSE PER BODY WEIGHT FOR ADULTS (mg per kg)

| Adult Dosing [mg/kg] | Component Preventative | | | |
|---|---|---|---|---|
| | Broad Range mg/kg | Preferred Range mg/kg | Preferred Amount mg/kg | Substitution Category mg/kg |
| ACTIVE INGREDIENTS | | | | |
| artemisinin | 22.68-54.43 | 40.82-49.89 | approx 45.36 | |
| berberine | 158.76-453.60 | 272.15-408.23 | approx 362.87 | |
| BLENDED MIXTURE* | 0-226.80 | 136.08-226.80 | approx 158.76 | Excipient with Active Ingredients |
| INERT INGREDIENTS | For binding or delivery of other ingredients. | | | |
| microcrystalline cellulose | 0-294.83 | 181.94-294.83 | approx 244.94 | Binders and compaction |
| stearic acid | 0-181.44 | 90.72-181.44 | approx 136.08 | Lubricant excipient |
| silicon dioxide | 0-22.68 | 13.61-22.68 | approx 18.14 | Water reducing agent and to promote absorption of water and prevent caking and clumping |
| calcium carbonate | 0-498.95 | 362.89-498.95 | approx 453.59 | Inert filler |
| magnesium stearate | 0-40.82 | 27.22-40.82 | approx 34.02 | For lubricating properties & to prevent powdered component from sticking to pill press equipment during compression from powder into solid tablets |
| croscarmellose sodium | 0-22.68 | 15.88-22.68 | approx 18.14 | To reduce water solubility and allow the material to expand, absorbing many times its weight in water and removing much of the water from Berberine. |

TABLE VIIA

Preventative Composition for Children in mg per pill

| Children Dosing [mg/Pill] | Component Preventative | | | |
|---|---|---|---|---|
| | Broad Range | Preferred Range | Preferred Amount | Substitution Category |
| ACTIVE INGREDIENTS | | | | |
| artemisinin | 12.5-30 mg | 22.5-27.5 mg | approx 25 mg | |
| berberine | 87.5-250 mg | 150-225 mg | approx 200 mg | |
| BLEND MIXTURE* | 0-200 | 150-200 | approx 175 mg | Excipient with Active Ingredients |
| INACTIVE INGREDIENTS | | | | |
| peppermint | 0-70 | 35-70 | approx 50 | Flavoring |
| xylitol | 0-1200 | 800-1200 | approx 1000 | Sweetener |
| 83% maltodextrin and 17% natural flavors | 0-120 | 80-120 | approx 100 | Masking Agent |
| Sucralose | 0-12 | 8-12 | approx 10 | Sweetener |
| INERT INGREDIENTS | | For binding or delivery of other ingredients | | |
| silicon dioxide | 0-220 | 160-220 | approx 200 | Water reducing agent that promotes absorption of water and prevents caking or clumping |
| calcium carbonate | 0-1200 | 800-1200 | approx 1000 | Inert filler |
| precipitated silica | 0-29 | 23-29 | approx 26.66 | Anticaking, free flow agent |

Approximately is defined as +/−5% in order to cover manufacturing variances and dosing tolerances.

In the tables, a gel cap example can consist of only artemisinin and berberine in the amounts referenced in the above tables.

*The blend mixture can consist of a blended mixture approximately 400 mg of concentrate of black walnut (*Juglans nigra*) dry outer hull; approximately 500 mg of concentrate of organically grown wormwood (*Artemisia absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

The inert ingredients are not therapeutic and are designed for the integrity, palatability and stability of the tablets. There are many substitutes for the various classes of inert ingredients that can include disintegrants, lubricants, binders, and excipients. The following classes can include but are not limited to:

Disintegrants can include but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating agents or Desiccating Agents can include but are not limited to sodium carboxy methyl cellulose, silica gel, microcrystalline cellulose, carboxymethylcellulose calcium, cellulose, colloidal silicone dioxide, and crosscarmellose Sodium.

TABLE VIIB

DOSE PER BODY WEIGHT FOR CHILDREN (mg per kg)

| Childrens Dosing mg/kg | Component Preventative | | | Substitution Category |
|---|---|---|---|---|
| | Broad Range mg/kg | Preferred Range mg/kg | Preferred Amount mg/kg | |
| ACTIVE INGREDIENTS | | | | |
| artemisinin | 5.67-13.61 | 10.21-12.47 | approx 11.39 | |
| berberine | 39.69-113.40 | 68.04-102.06 | approx 90.72 | |
| BLEND MIXTURE* | 0-226.80 | 136.08-226.80 | approx 158.76 | Excipient with Active Ingredients |
| INACTIVE INGREDIENTS | | | | |
| peppermint | 0-31.75 | 15.88-31.75 | approx 22.68 | Flavoring |
| xylitol | 0-544.31 | 362.87-544.31 | approx 453.60 | Sweetener |
| 83% maltodextrin and 17% natural flavors | 0-54.43 | 36.29-54.43 | approx 45.36 | Masking Agent |
| sucralose | 0-5.44 | 3.63-5.44 | approx 4.54 | Sweetener |
| INERT INGREDIENTS | For binding or delivery of other ingredients | | | |
| silicon dioxide | 0-99.79 | 72.57-99.79 | approx 90.72 | Water reducing agent that promotes absorption of water and prevents caking or clumping |
| calcium carbonate | 0-544.31 | 362.87-544.31 | approx 453.60 | Inert filler |
| precipitated silica | 0-13.15 | 10.43-13.15 | approx 12.09 | Anticaking, free flow agent |

Approximately is defined as +/−5% in order to cover manufacturing variances and dosing tolerances.

In the tables, a gel cap example can consist of only artemisinin and berberine in the amounts referenced in the above tables.

For children, defined as persons between the ages of 2 and 12 with a body weight below 110 pounds, the dosage is two tablets per day with a meal for 7 to 14 days depending on the number of days desired to stay parasite free. Two tablets provides 50 mg of artemisinin or one-half the adult dose. Tablets may be chewed or dissolved in the mouth. Two chewable tablets per day for 7 to 14 days is effective for preventing infection for 30 to 60 days, respectively. In addition to preventing malaria, the dosage regimen is appropriate for prevention of dengue fever, dysentery and yellow fever.

A dosage of two capsules a day for 14-28 days is effective for preventing Lyme disease and or babesiosis for 30 to 60 days, respectively.

Thus, someone skilled in the art makes a judicious selection of an appropriate dosage regimen; selection is dependent on the age or body weight of the patient, condition to be treated and the judicious selection is not a limitation of the present invention.

Methods of Manufacturing Tablets, Pills and Capsules

Our product by design and claim states a "passively accurate dosing system." Our manufacturing claims stated herein make it extremely possible to maintain and honor those claims. However, one can never preclude the possibility of the existence of some variance when mixing powdered compounds under high pressure. Although the FDA (stated in a 2004 letter from Dr. Steven Galson, then director of the Center for Drug Evaluation and Research at the FDA and now U.S. Surgeon General, that −20/+25%, "actually represents the acceptable bounds on the 90% confidence intervals around the ratio of the mean result for products") accepts those high deviations as normal, our concern was for tolerances at those extreme limits. However, while we believe there to be a reasonable amount of efficacy and safety at these extremes; we do not expect to exceed plus or minus 5% of our stated ingredient values.

Before the two active ingredient raw materials are accepted by the manufacturing laboratory, a chemical analysis of the composition is performed by an independent, third party commercial laboratory. This analysis confirms the purity of the materials as well as other compounds that might be present in the shipment. Industry standards for purity and other compounds are known and used to accept or reject a shipment.

Once the product is manufactured but before it is packaged, random batch samples are sent to another independent, third party commercial analysis laboratory where the pills are inspected and broken down to determine their contents. The dosing amounts are maintained as stated on the packaging, and the pills must be free of any contaminants. Failure to obtain the analysis laboratory approval results in a rejection of the batch.

In the Examples below, two types of compounds previously identified as anti-malarial agents are combined into one single pill. Artemisinin is a plant-based terpenoid compound that is known for use as an anti-malarial agent. Berberine is a plant-based alkaloid with a very bitter taste and water content in a range of approximately 14 wt. %. Successful bonding and adhesion through use of non-active ingredients is essential in order to produce a compressed physically stable pill. Adding granulation steps to the process reduces water and subsequently reduces the amount of non-active ingredients or excipients needed.

In addition, the manufacturing process solves the problem of keeping the formulated pill from becoming hydrated during shipment and storage in tropical climates by using blister packing immediately at the end of processing to maintain chemical composition and stability.

Methods of making an adult tablet and a chewable tablet will be described in examples 1 and 2 below.

Example 1

Method of Making an Adult Tablet

Calculate the weight for total production based on raw materials of artemisinin and berberine that are combined in a weight ratio of 1:8 or 100 mg of artemisinin to 800 mg of berberine.

In a V-Blender, mix the active ingredients, artemisinin and berberine at a low speed, i.e., 15 rpm, for 25 minutes to insure dispersal. Then add the non-active ingredients to the V-Blender in the following order: 540 mg microcrystalline cellulose, 40 mg silicon dioxide, 300 mg stearic acid, 1,000 mg calcium carbonate, 75 mg magnesium stearate, 40 mg croscarmellose sodium and continue blending for an additional 20 to 30 minutes.

Remove the mixture of active and non-active ingredients from the blender and filter through a 20 mesh screen, followed by filtering through a 100 mesh screen. After filtering through the 100 mesh screen, an oscillating granulator is used to granulate the mixture by feeding through a 45 rpm feed screw onto roller compactor (knurled rollers: 200 mm×50 mm) rollers set on low speed (15 rpm). Production of chips is the desired physical state after granulation.

Feed the granulated mixture into a tablet press; set to 8 US tons of pressure, at a speed of 900 rpm to produce tablets. Clean and vacuum the pills, so that no dust is present.

The cleaned and vacuumed pills are then placed in a coating machine (food grade pharmglaze). An enteric shell coating is applied. Coating is critical as a barrier to re-hydration and resists changes due to humidity found in the mostly equatorial destinations for the pills and temperature fluctuations in air cargo shipments. The coating is critical to preserving dosage integrity.

Following the coating of the pills, they are heated and tumbled at 45 degrees C. for 30 minutes. The heated and tumbled pills are than packaged immediately (within 24 hours) in a blister pack that is known in the art to prevent re-hydration and deterioration.

Example 2

Method of Making a Chewable Pill for Children

The method for making the adult tablet is used for making a chewable pill with the following adjustments to active and non-active ingredients. First, the active ingredients artemisinin and berberine are combined in a weight ratio of 1:8 or 25 mg of artemisinin to 200 mg of berberine. The non-active ingredients added to the blender include flavorings and sweeteners and a masking agent to make the pill palatable so that ill children will chew and swallow the composition.

More specifically, in a V-Blender, the active ingredients, artemisinin and berberine are blended at a low speed for 25 minutes to insure dispersal. Then the non-active ingredients are added to the V-Blender in the following order: 50 mg peppermint flavoring, 1000 mg xylitol, 100 mg masking agent (a mixture of 83% maltodextrin and 17% natural flavors), 10 mg sucralose, 26.66 mg precipitated silica, 1000 mg calcium carbonate, 200 mg silicon dioxide and continue blending for an additional 20-30 minutes. Sucralose and xylitol are natural sweeteners that do not raise blood sugar levels and add no caloric value.

The processing steps are the same as in Example 1 after removal of the active and non-active ingredients from the V-Blender.

Prior to the present invention, it was not known to combine artemisinin and berberine and in a single pill, tablet or capsule in the specific weight ratios disclosed. It was also not known that this combination of active ingredients could successfully treat and prevent infectious diseases such as, but not limited to, malaria, dengue fever, dysentery, yellow fever, Lyme disease, babesiosis, progressive multifocal leukoencephalopathy, *Helicobacter Pylori*, and colitis. It is also significant that the formulation of the present invention contain no quinine or quinine derivatives. The artemisinin and berberine compositions of the present invention can be expected to transform medical care and dramatically reduce illness and death from infectious diseases and infection-causing bacterial strains that have developed resistance to antibiotics.

In addition to therapeutic benefits, the present invention solves the problem of incorrect dosages by self-administering patients, inaccurate combining of ACTs which leads to non-therapeutic results, and a chewable form of tablet or pill agreeable to children.

Table VIII shows pediatric doses shipped to foreign countries for testing doses for various treatments as of Oct. 1, 2012.

TABLE VIII

Shipped Quantity - Pediatric Doses

| Countries | Cholera | Dengue | Malaria | Grand Total |
|---|---|---|---|---|
| Ghana | | | 100 | 100 |
| Guatemala | | 25 | | 25 |
| Haiti | 15 | | | 15 |
| Honduras | | | 5 | 5 |
| Kenya | 5 | | 5 | 10 |
| Liberia | 2 | | 19 | 21 |
| Marshall Islands | | 5 | | 5 |
| Nicaragua | | 20 | 55 | 75 |
| Nigeria | | 100 | 2 | 102 |
| Philippines | 25 | 35 | 5 | 65 |
| Puerto Rico | | 5 | 5 | 10 |
| Thailand | | 5 | | 5 |
| Togo | | | 110 | 110 |
| Zimbabwe | 5 | | | 5 |
| Grand Total | 52 | 195 | 306 | 553 |

Table IX shows adult doses shipped to foreign countries for testing various treatments as of Oct. 1, 2012.

TABLE IX

Shipped Quantity - Adult Doses

| Countries | Cholera | Dengue | Malaria | Grand Total |
|---|---|---|---|---|
| Brunswick | 20 | | | 20 |
| Ghana | | | 200 | 200 |
| Guatemala | | 50 | | 50 |
| Haiti | 25 | | | 25 |

TABLE IX-continued

| Countries | Shipped Quantity - Adult Doses | | | |
| --- | --- | --- | --- | --- |
| | Cholera | Dengue | Malaria | Grand Total |
| Honduras | | 10 | 5 | 15 |
| Kenya | 5 | | 5 | 10 |
| Liberia | 2 | | 34 | 36 |
| Marshall Islands | | 15 | | 15 |
| Nicaragua | | 320 | 110 | 430 |
| Nigeria | | 200 | 2 | 202 |
| Philippines | 50 | 100 | 10 | 160 |
| Puerto Rico | 50 | 10 | 10 | 70 |
| Thailand | | 10 | | 10 |
| Togo | | | 220 | 220 |
| Zimbabwe | 5 | | | 5 |
| Grand Total | 157 | 715 | 596 | 1468 |

The various patients from Case Studies residing in the US are available for direct contact and verification Malaria A nongovernmental organization (NGO) asked the inventors if they could bring malaria treatment samples with them on their mission trips. We agreed with the understanding that if they used the samples, they would send field reports back of their experiences. The following are the field reports we received from Ghana:

Malaria Field Report #1
Patient's Name: Hodzinya R.
Date: 28 Jan., 2012
Age of patient: 40
DAY ONE of coACT A-B Malaria Therapy
two tabs in the morning and two in the evening were taken and the bitter saliva still persisted, but felt feverish for the greater part of the day and felt very weak
DAY TWO of coACT A-B Malaria Therapy
The same dosage and the feverish condition stopped and [the patient] started eating slowly, but the weakness was reported
DAY THREE of coACT A-B Malaria Therapy
One tablet in the morning. The weakness was gone and bitter saliva also was gone.
DAY FOUR OF coACT A-B Malaria Therapy
The last tablet was taken in the morning and the heat and feverish condition were gone. Appetite regained.
Malaria Field Report #2
Patient's Name: Angela A.
Date: 28 Jan., 2012
Age of patient: 24
DAY ONE of coACT A-B Malaria Therapy
two tabs in the morning and two in the evening were taken and the bitter saliva still persisted, but felt feverish and could not drink water
DAY TWO of coACT A-B Malaria Therapy
The same dosage and the feverish condition stopped and started drinking slowly, but the weakness was reported. She was not feeling comfortable in her stomach
DAY THREE of coACT A-B Malaria Therapy
One tablet in the morning. The weakness was gone, stomach upset gone, and bitter saliva also was gone.
DAY FOUR of coACT A-B Malaria Therapy
The last tablet was taken in the morning and the heat and feverish condition were gone. Appetite regained for both water and food.
Malaria Field Report #3
Patient's Name: Prosper A.
Date: 28 Jan., 2012
Age of patient: 36
DAY ONE of coACT A-B Malaria Therapy
two tabs in the morning and two in the evening were taken and the bitter saliva still persisted, but he felt feverish and could not eat/drink water
DAY TWO of coACT A-B Malaria Therapy
The same dosage and the feverish condition subsided and started drinking slowly. He was not feeling very well then
DAY THREE of coACT A-B Malaria Therapy
One tablet in the morning. The feverish condition was gone, feeling quite well, and bitter saliva also was gone.
DAY FOUR of coACT A-B Malaria Therapy
The last tablet was taken in the morning and the heat was gone. Appetite regained. For both water and food.
Malaria Field Report #4
Patient's Name: Mawusi A.
Date: 28 Jan., 2012
Age of patient: 28
DAY ONE of coACT A-B Malaria Therapy
two tabs in the morning and two in the evening were taken but the bitter saliva still persisted, and she felt feverish and loss of appetite
DAY TWO of coACT A-B Malaria Therapy
The same dosage and the feverish condition subsided and appetite was restored. The heat persisted
DAY THREE of coACT A-B Malaria Therapy
One tablet in the morning. The feverish condition was gone, the heat was gone, feeling quite well, and bitter saliva also was gone.
DAY FOUR of coACT A-B Malaria Therapy
The last tablet was taken in the morning and the heat was gone. Appetite regained for both water and food. She lost some weight
Malaria Field Report #5
Patient's Name: Davigah D.
Today's Date: 28 Jan., 2012
Age of patient: 40
DAY ONE of coACT A-B Malaria Therapy
two tabs in the morning and two in the evening were taken and the bitter saliva was tamed, but she felt feverish for the greater part of the day and felt dizzy
DAY TWO of coACT A-B Malaria Therapy
The same dosage and she somehow regained appetite and started eating slowly, but the knees were shaking.
DAY THREE of coACT A-B Malaria Therapy
One tablet in the morning. The dizziness was gone and also the shaking
DAY FOUR of coACT A-B Malaria Therapy
The last tablet was taken in the morning and the heat was gone and she was able to drink enough water and ate quite well.

Case studies for dengue fever, Lyme disease, *Helicobacter Pylori* (HP), colitis will now be described.

Dengue Case Study #1

21-year-old young lady named Carla, who works as a nurse at a local clinic. Carla was diagnosed with Dengue through confirmation of a urine test and a blood test. She was in terrible pain and vomiting when her fever elevated, which hovered over 102 degrees Fahrenheit. This went on for several days until she took her first day's treatment of coACT A-B for Dengue Fever. Within one day, her vomiting had stopped, but more importantly, the crippling pain that ran through her body had also subsided. Carla was needed back at work, but still feeling tired. Her second day's treatment brought brighter results and she began to feel like herself again with all symptoms gone.

Lyme Disease—Case Study #1

Shawn F. is a 48-year-old Caucasian female, who is 5'4" and weighs 200 lbs. She is a full-time registered nurse, and lives in the United States. Her first symptoms appeared in September of 2008. When Shawn was first diagnosed with Lyme disease she had the tell-tale "target" lesion and was prescribed 10 days of the antibiotic doxycycline. She was diagnosed by her husband (a full-time practicing Physician's Assistant) and herself. Her disease progressed to Stage 2 Lyme due to inadequate Stage 1 treatment. Her doctors did not diagnose Stage 2 because she had been given antibiotics during the initial stage, and they believed that would rid her of Lyme disease. However, her doctors soon observed blindness, arthritis, and severe photophobia. Shawn was examined by 14 different specialists, in part because of her occupation in the health care industry; her physicians included internists, infectious disease specialists, tropical diseases specialists, and others.

After many diagnoses and treatments that did not assuage her symptoms, Shawn was desperately searching for something to ease her constant pain and disability. Unfortunately, she had been misdiagnosed so many times that the disease had time to spread throughout her body, further progressing to becoming tertiary and causing severe pain, debilitating migraines, and near-total vision loss. Shawn could no longer practice nursing. She was confined to her home; hers was a dark, shuttered existence, since exposure to even the slightest light triggered severe migraines. Depression and thoughts of suicide plagued her. It was at this point that she took her first dosage of coACT A-B; immediately her arthritis and photophobia improved but the blindness remained. She maintained a Lyme diet, followed the dosing as written, was not taking any other medications intended for Lyme disease, and experienced no side effects. Shawn has since returned to practicing nursing again, and credits coACT A-B with much of her recovery.

Case Study #2—Lyme Disease

Kathy T. is a 41-year-old Caucasian female, who is 5'1" and weighs 153 lbs. She worked as a full-time project manager for a non-profit food bank, and lives in the United States. Her symptoms first appeared in August of 2010. When Kathy was first diagnosed she had skin rashes that were not helped with topical treatments, low-grade fevers, severe migraines, continuous muscle aches, sore throat, stomach pain, joint pains, gynecological issues, and constant fatigue. The initial indication was hives on her stomach and back which grew to circular rashes on both thighs, all directly following an insect bite from what she believes to have been a horse fly.

Kathy sought and received treatment from a gynecologist, an acupuncturist, a primary care physician, a chiropractor, a massage therapist, two neurologists, a rheumatologist, an ENT, a nurse practitioner, and a naturopath. From these professionals she was diagnosed not only with Lyme disease, but the following diagnoses and/or misdiagnoses: fibromyalgia, depression, arthritis, pinched nerve, burning mouth syndrome, and mycotoxic poisoning. By May 2011 she was confirmed with Lyme disease and subsequently reconfirmed by another physician in August 2011. Her case of Lyme disease was clinically diagnosed based on lab findings, Western Blot, and symptomatology. Kathy further tested positive for *Ehrlichia* via Igenix lab test, as well as on Lyme tithers 41, 23, and 39, Epstein Barr, Parvo, M. Pneumoniae, HHV 6, and Cytomegalovirus (common co-infections of Lyme), and high C4a and CD57 numbers. Kathy was initially prescribed a 45-day regimen of Doxycycline, which helped eliminate her then inability to talk and walk. Additionally, she was given Nystatin and vitamins, neither of which made any detectable difference. Acyclovir caused her symptoms to worsen in that she could not lift her arms. GU treatment (Chinese herbs) helped her for a couple of months and then stopped working. Ivermectin and Pyrantal Pamoate helped her to pass parasites in her stool, but left her lifeless, dizzy, and with nystagmus. Intravenous Rocephin administered three times per week for four weeks helped restore her energy, but caused an allergic reaction. Tindamax was likewise not tolerated. Albendazole seemed to help her with passing parasites. Other anti-fungals caused pain and further reduced her energy levels.

Kathy was taking Albendazole during the initial phase of her coACT A-B dosing, and she followed the dosing that was given to her in April of 2012. Her side effects (muscle tremors at night) dissipated within the first week of dosing. Kathy experienced a significant increase in energy and stamina, which improved her overall condition in ways she had not experienced since contracting Lyme disease. She reported climbing the lighthouse stairs in St. Augustine, Fla. without suffering a decrease in energy afterwards, which was atypical for her at that time. She reported waking up early, and feeling refreshed, which she said was far from the norm for her; since she was not taking any other medications at the time, she attributes it entirely to coACT A-B. Her arthritic arm pain had also diminished significantly within four days of taking coACT A-B; she described the pain in her arms as having gone from a high of 7-8 on the pain scale to a low of 1-2. She also reported passing some odd snail-like items in her stool, which in itself was not unusual for her, but she believes that these were different, almost slug-like, and Kathy stated that afterwards she felt as though she had expelled "something poisonous." Upon further exams and testing, her HHV-6 had dropped from 25.38 to 4.8, producing the first positive change Kathy had seen in any of her virus lab tests during the past two years. Kathy has stated that coACT provided her with "a few really good weeks which is invaluable when you haven't functioned normally for some time. For chronic long-term patients, I suspect additional dosing (like every few months or so) is necessary. For newcomers or uncomplicated cases, it could be a bridge to health and healing.

Lyme Disease—Focus Group Survey Results

Subsequent results based on Focus Group responses from a group of 18 Lyme patients taking the dosing over a 24 day period.

FIG. 1 is a graph of a Lyme focus group survey results for rating quality of life. This shows periods of improvement in the quality of life during both dosing phases and regression during the period of no dosing.

Figure 2:
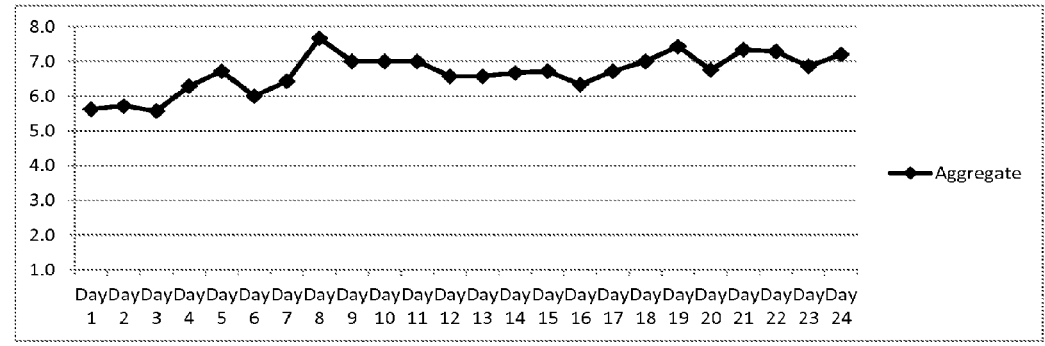
FIG. 2 is a graph of Lyme focus group survey results requesting participants to rate how easy it is to bend, kneel or stoop.

FIG. 2 is a graph of Lyme focus group survey results requesting participants to rate how easy it is to bend, kneel or stoop. This shows an 28% improvement in leg mobility throughout the dosing schedule.

Figure 3:
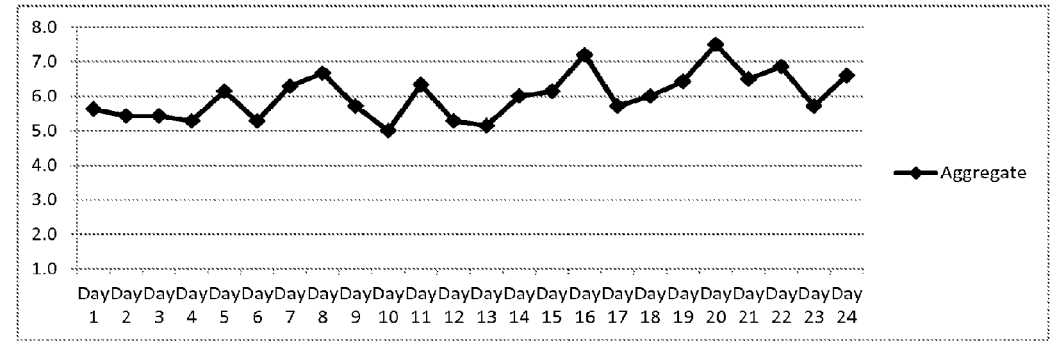
FIG. 3 is a Lyme focus group survey results for rating everyday activities.

FIG. 3 is a Lyme focus group survey results for rating everyday activities. This shows fluctuations in improvement for activities of daily living. The trend overall from beginning to end of dosing shows 17% improvement.

Figure 4:
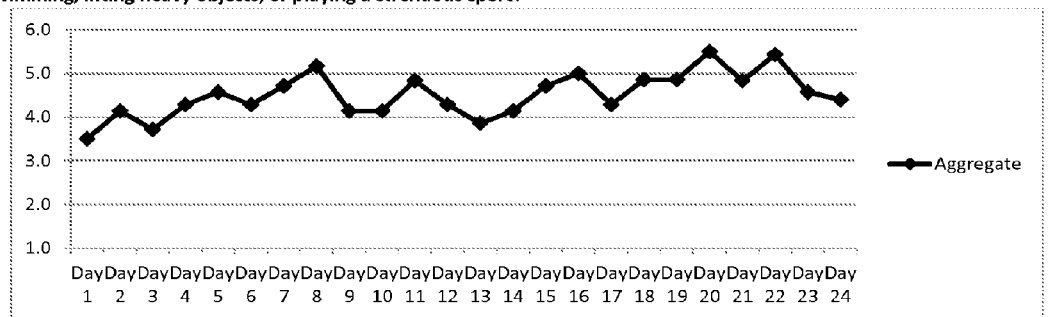
FIG. 4 is a Lyme focus group survey results for rating vigorous activities.

FIG. 4 is a Lyme focus group survey results for rating vigorous activities. This shows moderate improvement in strenuous activities. This is the category that started with the lowest baseline, so the overall improvement of 25.7% was significant.

Figure 5:
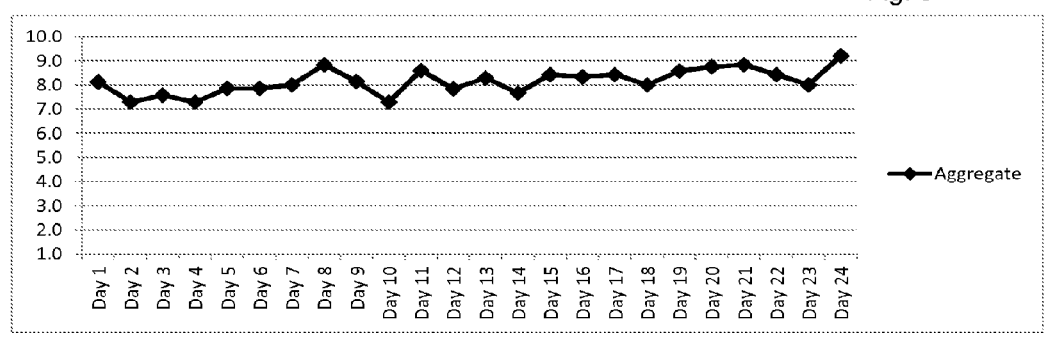
FIG. 5 is a Lyme focus group survey results for rating bath, shower and dress capability.

FIG. 5 is a Lyme focus group survey results for rating bath, shower and dress capability. This shows 13.2% improvement in ability to bathe and dress.

Figure 6:
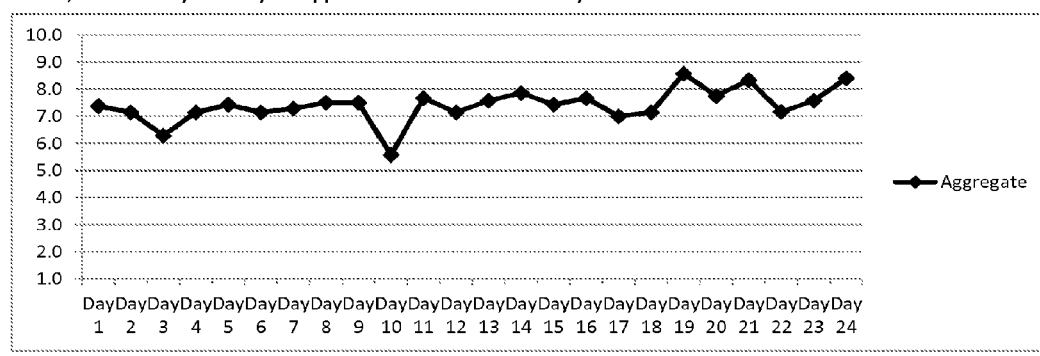
FIG. 6 is a Lyme focus group survey results for rating appetite and food consumption.

FIG. 6 is a Lyme focus group survey results for rating appetite and food consumption. This shows 13.9% improvement in appetite and ability to consume food.

Figure 7:
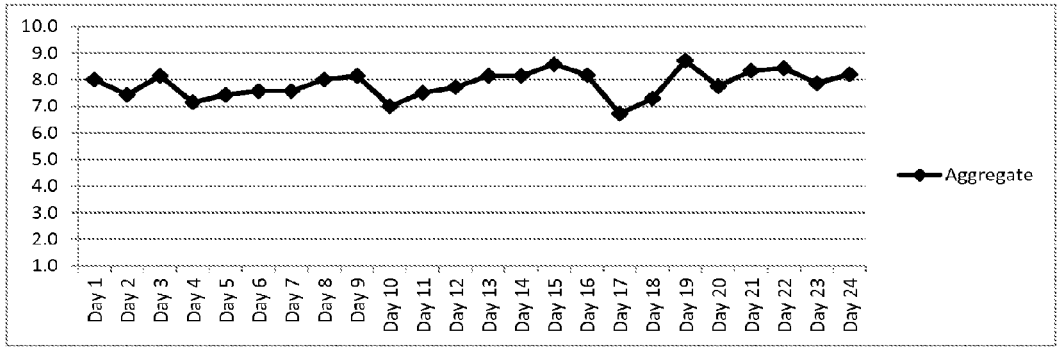
FIG. 7 is a Lyme focus group survey results for rating intake of fluids.

FIG. 7 is a Lyme focus group survey results for rating intake of fluids. This generally shows minimal impact on ability to consume fluids. 2.5% improvement is not statistically significant Testing Procedures to determine the Pill.

Figure 8:
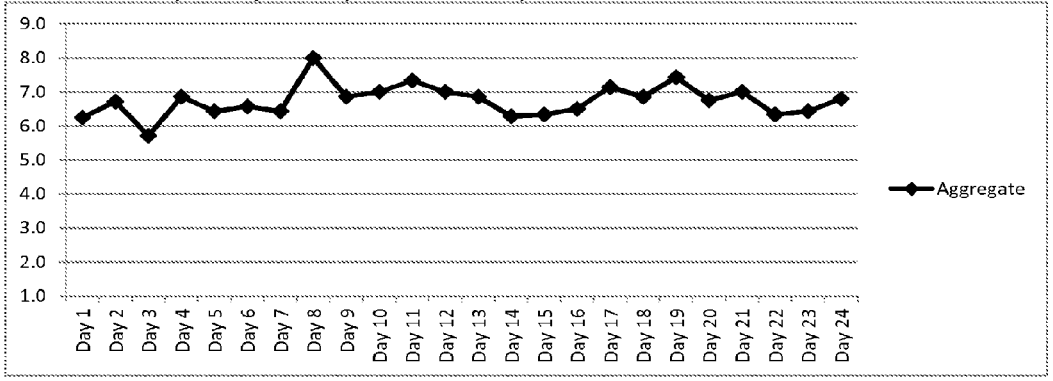
FIG. 8 is a Lyme focus group survey results for rating ability to move and turn neck.

FIG. 8 is a Lyme focus group survey results for rating ability to move and turn neck. This shows some early improvement during the first week of dosing, with some regression in progress but overall 8.8% improvement from baseline.

Figure 9:
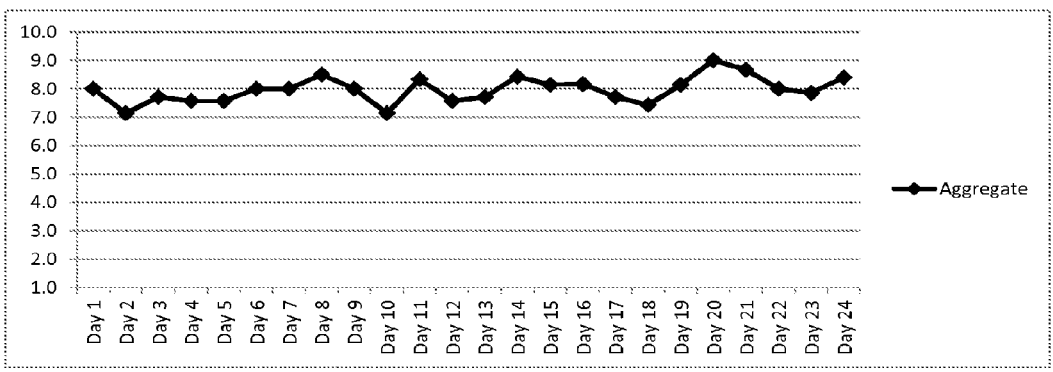
FIG. 9 is a Lyme focus group survey results for rating ability to sit upright and do activities.

FIG. 9 is a Lyme focus group survey results for rating ability to sit upright and do activities. This shows some moderate improvement towards the end of the dosing schedule in ability to sit while performing daily activities. Overall improvement is 5%.

Figure 10:
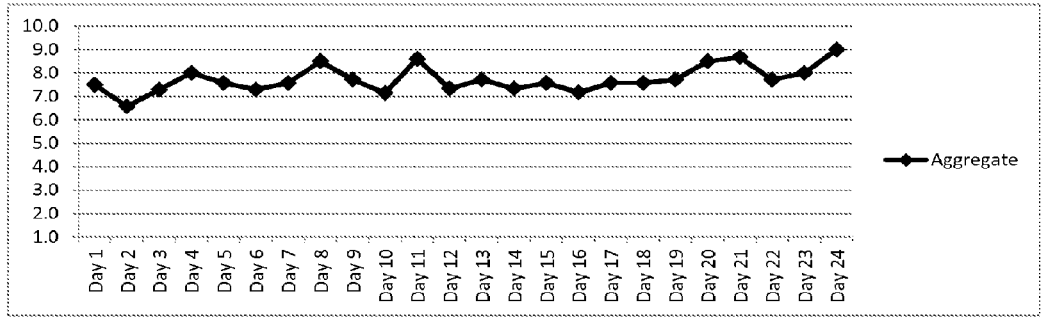
FIG. 10 is a Lyme focus group survey results for rating sensitivity to light.

FIG. 10 is a Lyme focus group survey results for rating sensitivity to light. Light sensitivity is a common issue for Lyme patients. This showed an overall 20 improvement in sensitivity to light.

Figure 11:
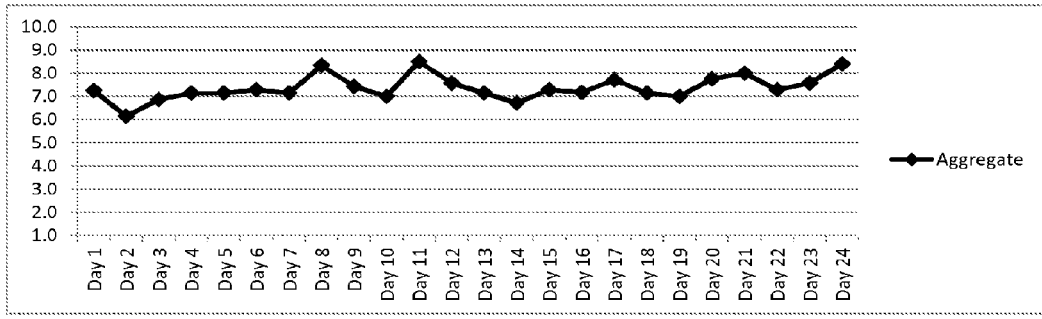
FIG. 11 is a Lyme focus group survey results for rating sensitivity to sound.

FIG. 11 is a Lyme focus group survey results for rating sensitivity to sound. Overall improvement in sensitivity to sound 15.9%

Figure 12:
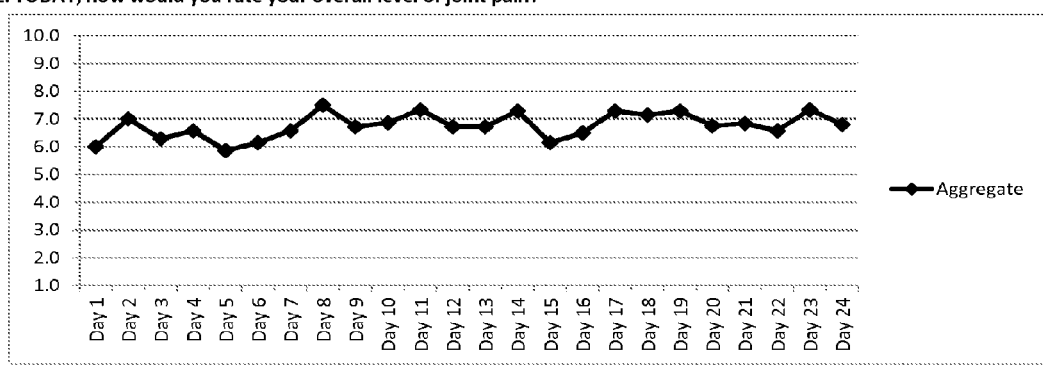
FIG. 12 is a Lyme focus group survey results for rating overall level of joint pain.

FIG. 12 is a Lyme focus group survey results for rating overall level of joint pain. Joint pain may be caused by accumulation of dead spirochetes. Overall improvement in joint pain was 13.3%

Figure 13:
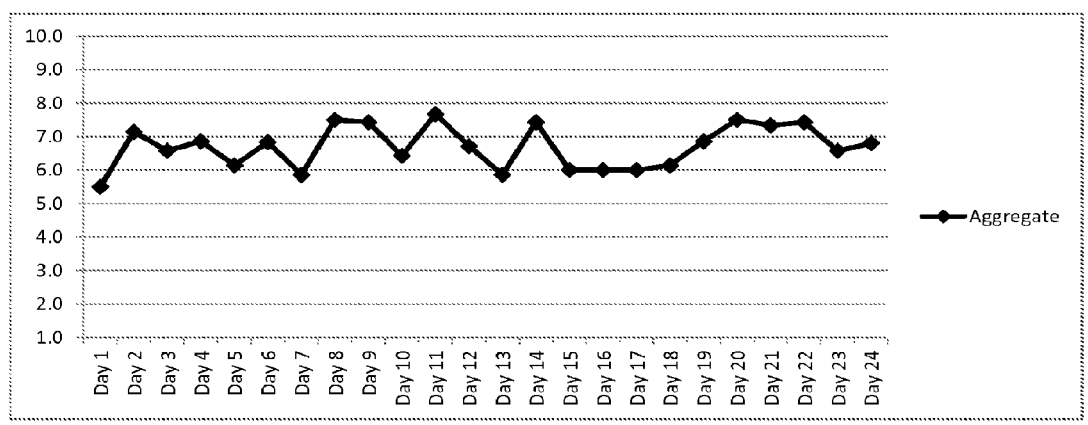
FIG. 13 is a Lyme focus group survey results for rating overall mood.

FIG. 13 is a Lyme focus group survey results for rating overall mood. This was one of the most significant areas reported for improvement. Overall mood improved 23.6% during the course of the dosing.

*Helicobacter Pylori* (HP) Case Report #1

Melissa D. is a 61-year-old Caucasian female, who is 4'11" and weighs 147 lbs. She is an antiques and collectibles dealer, selling full time in a store location as well as on-line, and lives in the United States. Melissa's first symptoms appeared when she was in her late 20's; at that time she was diagnosed with a duodenal ulcer. Shortly after what appeared to be a successful recovery, a deep tissue biopsy in 1989 revealed that she suffered from systemic lupus. She was treated with steroids but did not tolerate them very well. A program was developed that included Shark Cartilage, Fish Oil, and DHEA; Melissa followed this program successfully and the lupus went into remission within three months. Decades later, she continues to maintain her diet and intake of the three supplements in order to keep the lupus in check.

Her first diagnosis of *Helicobacter Pylori* was in the 1990's, and her treatment has included Proton Pump Inhibitors (PPI), as well as Choline, Inositol, Serrapeptase, and Hesperidin, as well as monitoring her diet, but not in according to any regular schedule. She continues to be monitored and cared for by two physicians, an MD and a DO, who both give her a poor prognosis of leading a normal life in terms of digestive health. She is frequently deprived of energy, lacks stamina to perform daily household chores, and is always anxious regarding access to bathroom facilities when she is in an unfamiliar location.

Melissa was prescribed several PPI's, but finds their effectiveness diminishing with each successive administration. She tries to maintain a sense of normalcy by restricting her diet, reducing stress where she can, and undertaking a modest exercise program. She suffers from acute HP almost once a week in spite of her efforts.

Before her coACT A-B trial began, Melissa stopped taking any other medications or supplements for a full week. By the second day of dosing Melissa experienced more vigor and better sleep than she had in many years. She went off her diet (because she felt absolutely no twinges or signals of an impending attack), eating as she pleased for the first time in several years. Her diet became totally contradictory to what has been advised and prescribed to her, and included such risky fare as fried chicken, store-made tacos, and chocolate. Normally any one of these foods would trigger a severe attack; however, Melissa states she has not experienced a single attack since she began taking coACT A-B. Melissa's dosing regimen followed an alternative "pulse" plan that we recommended to her. She took two pills a day for Days One and Two, followed by one pill a day for eight more days. This was followed by an "off" period of 8 days where she took no coACT A-B at all, which was then followed by eight more days of taking one coACT A-B tablet per day. This trial was September of 2012. Melissa has, as of this date of filing, not experienced another acute attack of HP; in fact, she does not sense any of her previous symptoms. She did not note any side effects during his trial or in the time thereafter that we have collected her follow up data (October 2012).

Colitis Case Report #1

Jim G. is a 60-year-old Caucasian male, who is 5'11" and weighs 212 lbs. He is a full-time logistics professional who lives in the United States. Jim's first symptoms appeared in June 2001, following an overseas trip to Vietnam. While in Vietnam, Jim became seriously ill and was unable to continue the scheduled trip, returning immediately to the United States. His family doctor examined him and sent him to a gastroenterologist who, after performing several tests, diagnosed Jim's illness as *Campylobacter jejuni*. Since that time Jim has suffered violent stomach cramps, usually with no advance warning. Subsequent to that first event, and upon additional clinical examinations and testing by his physician, including stool samples, blood tests, and a colonoscopy, Jim has been diagnosed with mild colitis.

Jim was prescribed aminosalicylates and steroids by his doctor; both medications are in pill form, with a dosage of four pills to be taken three times daily. Jim found that he could not tolerate either of the two prescriptions, which often left him with as much pain as the colitis itself caused. For the past eight years Jim has elected not to take prescription drugs to treat his colitis, instead submitting to and accepting the attacks of colitis which occurred, on average, once a month.

During his coACT A-B trial, Jim was not taking any medicine for colitis, nor was he taking any other digestive aid. Jim began his trial of coACT A-B while suffering from a colitis attack; he was experiencing severe acute stomach pain before he took his first dose. After the first dose Jim felt some relief and by the second day, his acute stomach pain was relieved. Jim followed the dosing on the package (two pills a day for Day One and Day Two, followed by one pill a day for eight days) and remained on the treatment for a full 10 days. This episode was in mid-January, 2012. As of this date of filing, Jim has not experienced another attack of colitis. He did not note any side effects during his trial or in the time thereafter that we have collected his follow-up data (October 2012).

Colitis Case Report #2

Angie L. is a 43 year old Caucasian female, who is 5'6" and weighs 185 lbs. She is an information technology professional with her own company, and lives in the United States. Her first symptoms appeared in her early teens with bouts of diarrhea; these began as random bouts at age 13, becoming increasingly frequent until by the age of 16 they were nearly a daily occurrence. Her parents brought her to a pediatrician, who recommended dietary changes. She began by eliminating chocolate, then sugar, then soft drinks, then caffeine in both liquids and solids. After additional examinations and counseling, the pediatrician attributed her condition to stress, describing it as a "nervous stomach." When Angie was 16, the pediatrician referred her to a gastroenterologist, as Angie was missing days of school more frequently as the bouts of diarrhea were worsening. She was given a colonoscopy; the results were relatively normal, and no polyps were found. She was prescribed Bentyl with instructions to use when acute attacks presented. At age 25, Angie was prescribed a series of tests by Dr. Keith Moore of Orlando, including colonoscopy and endoscopy, resulting in diagnoses of collagenous colitis and a duodenal ulcer. Since cases of this type of colitis were considered rare, a second opinion was obtained at the University of Florida Shands Hospital. There, the initial diagnosis was confirmed following a colonoscopy, endoscopy and additional extensive digestive tract testing.

Angie was prescribed drugs designed and intended to lower cholesterol; these medications were known to be effective in slowing down the effects of chronic diarrhea. She then switched to Asacol and Prevacid for several years, which was followed by Prevacid and other ulcer prescriptions. She did not tolerate many of the prescriptions well, as they usually resulted in severe stomach cramps. In 2001, Angie began taking Ultram to combat the mild arthritis and joint pain associated with the colitis, and the drug's side effects helped to curtail the pain for a few years. She was able to completely drop ulcer medications in 2003 and began taking Hyoscamine daily for the colitis.

After the Hyoscamine's effectiveness decreased, early in 2012, she began a course of coACT A-B. After taking two coACT A-B tablets a day for days one and two, she halved the dosage for the following eight days (one-half of a coACT tablet per day). She did experience stomach cramps and a "burning sensation" while taking coACT A-B, which she attributed to her ulcer. Angie's condition, since the age of 13, has always entailed 10 trips a day to the bathroom, and chronic diarrhea. At age 42, having taken coACT A-B, Angie reports that she now experiences normal BMs for the first time in nearly 30 years. Her colitis continues to present itself but she feels that her present condition, since taking coACT A-B, is better than anything she has experienced since the age of 13. Her bloating and cramping has steadily diminished, as has her sensitivity to certain foods. Since January 2012, when she began taking coACT A-B, to the date of this application (October 2012), Angie has no longer needed any daily medication.

Dengue Fever Results

Dr. Jamie Z. Galvez Tan MD, MPH, former Vice Chancellor for Research University of the Philippines and a known expert in the field, tested the efficacy of the invention combination of artemisinin and berberine for treating Dengue Fever. On Oct. 7, 2012, Dr. Galvez reported that "I am pleased to inform you of my staff's and my initial findings using the initial 200 sample doses you provided of coACT A-B Dengue Fever Formula. We have observed that coACT A-B is highly effective in relieving the symptoms of dengue fever patients, based on both clinical physical examinations and clinical measurements. We witnessed a uniform return to wellness— the ability to drink and increase in appetite, as well as desirable changes in patients' blood platelet levels—in as little as eight hours after the initial dosing. These results appear to indicate action against all four types of dengue fever."

Although the embodiments above describe the combination of artemisinine and berberine, the invention can include combinations of the derivatives of artemisinin with berberine. The deriviatives of artemisinin can include but are not limited to: artesunate, artemether, dihydroartemisinin, artelinic acid, artenimol, and artemotil. For example, the chemical weight of artesunate can be adjusted to give the same effective chemical yield as artemisinin, and artesnuante and berberine can then combined. Similarly, the chemical weight of artemether can be adjusted and combined with berberine.

Similarly, the chemical weight of dihydroartemisinin can be adjusted and combined with berberine. Similarly, the chemical weight of artelinic acid can be adjusted and combined with berberine. Similarly, the chemical weight of artenimol can be adjusted and combined with berberine. Similarly, the chemical weight of artemotil can be adjusted and combined with berberine.

Alternative ACT with Natural Botanical Active Ingredients for Treatment and Prevention of Chikungunva.

Chikungunya is a viral disease transmitted to humans by the bite of infected *Aedes Aegypti* mosquitoes. Chikungunya virus is a member of the genus Alphavirus, in the family Togaviridae. Other notable vector-borne alphaviruses in the United States primarily includes Eastern equine encephalitis virus and also to a much lesser extent, Western equine encephalitis virus. Chikungunya virus was first isolated from the blood of a febrile patient in Tanzania in 1953, and has since been identified repeatedly in West, Central and Southern Africa and many areas of Asia, and has been cited as the cause of numerous human epidemics in those areas since that time. The virus circulates throughout much of Africa, with transmission thought to occur mainly between mosquitoes and monkeys. Chikungunya has been described by both patients and attending physicians as a "cousin to malaria."

Although first isolated in Tanzania in 1952, it wasn't until more recently in 2004, that chikungunya virus spread throughout the larger portion of Africa and into the Central Asian Continent and Southeast Asia often causing large and sporadic epidemics in those regions.

The name "Chikungunya" is derived from the language of the Makonde ethnic groups in southeast Africa and means "that which bends" or "stooped walk." This is in reference to the hunched over appearance of individuals who are infected due to the characteristically painful and often times incapacitating arthralgia caused by the virus.

Until recently, chikungunya virus was primarily sequestered to Africa, Asia, and the Pacific islands. The first locally transmitted case in the Western Hemisphere, meaning that the index patient had not traveled to a chikungunya virus endemic region, occurred in December of 2013 on the island of St. Martin.

As of June 2014, over 165,000 suspected cases of chikungunya virus infection in the Western Hemisphere have been reported, of which over 4,500 have been confirmed by laboratory testing and these numbers are continuing to increase.

Importantly, indigenous or local transmission of chikungunya virus has not been reported in the United States or its territories, aside from Puerto Rico. And as of June 2014, the 57 reported US cases have thus far been associated with travel to endemic areas.

However, due to the widespread distribution of a competent mosquito vector in the United States and a naïve host population that has not yet been exposed to and lacks protective immunity to chikungunya virus, the possibility of chikungunya virus outbreaks in the United States is a very real public health threat.

Clinical Presentation:

Following transmission of the virus by the bite of an infected mosquito, the incubation period, prior to development of symptoms, ranges on average from 3 to 7 days. Unlike other mosquito-borne viruses like West Nile virus and dengue virus, the majority of individuals who are exposed to chikungunya virus become symptomatic, with the most severe manifestations observed at the extremes of age and in those with suppressed immunity. Importantly, however, it was once believed that exposure to chikungunya virus would allow individuals to develop lasting immunity and protection from re-infection. That belief is no longer held by the modern view, evidence of such as by what is currently being experienced in other Countries.

Also, fatalities due to chikungunya virus infection are uncommon, though they have been reported among elderly patients with significant underlying comorbidities or those with suppressed immune function.

Chikungunya virus infection can progress through 3 distinct stages, the acute, subacute, and chronic forms.

During the acute stage of infection, most individuals will experience a sudden onset, high fever along with severe and often incapacitating joint pain or polyarthralgia. The polyarthralgia is typically bilateral and symmetric, involving multiple joints, most commonly in the hands and feet. A fair percentage of patients will also present with a maculopapular rash involving the trunk and extremities that develops 2 to 5 days following fever onset.

Other less common symptoms include severe headache, myalgias, and back pain, and laboratory findings are fairly nonspecific, including thrombocytopenia, leukopenia, and elevated liver function tests. This stage of infection can last anywhere from 3 to 10 days, after which most patients will feel significant symptom relief and improvement.

The majority of people infected with chikungunya virus become symptomatic. The incubation period is typically 3-7 days (range, 1-12 days). The disease is most often characterized by acute onset of fever (typically >39° C. [102° F.]) and polyarthralgia. Joint symptoms are usually bilateral and symmetric, and can be severe and debilitating. Other symptoms may include headache, myalgia, arthritis, conjunctivitis, nausea/vomiting, or maculopapular rash. Clinical laboratory findings can include lymphopenia, thrombocytopenia, elevated creatinine, and elevated hepatic transaminases.

As stated previously, unfortunately, symptom relapse can occur in some individuals, most often reappearing 2 to 3 months following the initial infection. This is defined as the subacute stage and patients primarily experience rheumatic symptoms including exacerbation of pain in previously affected joints.

While most individuals will recover from the acute or subacute stages, for some patients, symptoms can persist for months to years following initial infection, leading to chronic rheumatism and fatigue. In studies from Africa and India, the percentage of individuals with chronic symptoms at 10 months postinfection varies from 12 to 50% with the elderly at greatest risk.

Acute symptoms typically resolve within 7-10 days. Rare complications include uveitis, retinitis, myocarditis, hepatitis, nephritis, bullous skin lesions, hemorrhage, meningoencephalitis, myelitis, Guillain-Barré syndrome, and cranial nerve palsies. Persons at risk for severe disease include neonates exposed intrapartum, older adults (e.g., >65 years), and persons with underlying medical conditions (e.g., hypertension, diabetes, or cardiovascular disease). Some patients might have relapse of rheumatologic symptoms (e.g., polyarthralgia, polyarthritis, tenosynovitis) in the months following acute illness. Studies report variable proportions of patients with persistent joint pains for months to years. Mortality is rare and occurs mostly in older adults.

Transmission:

Chikungunya virus is primarily transmitted to humans through the bites of infected mosquitoes, predominantly *Aedes aegypti* and *Aedes albopictus*. Humans are the primary host of chikungunya virus during epidemic periods. Bloodborne transmission is possible; cases have been documented among laboratory personnel handling infected blood and a health care worker drawing blood from an infected patient. Rare in utero transmission has been documented mostly during the second trimester. Intrapartum transmission has also been documented when the mother was viremic around the time of delivery. Studies have not found chikungunya virus in breast milk and there have been no reports to date of infants acquiring chikungunya virus infection through breastfeeding. Because the benefits of breastfeeding likely outweigh the risk of chikungunya virus infection in breastfeeding infants, mothers should be encouraged to breastfeed even if they are infected with chikungunya virus or live in an area with ongoing virus transmission.

The risk of a person transmitting the virus to a biting mosquito or through blood is highest when the patient is viremic during the first week of illness.

Regarding transmission, it's important to remember that humans are the primary reservoir for chikungunya virus and that *Aedes* species mosquitos are the primary vectors, with the viral life-cycle circling between these 2 hosts. *Aedes albopictus* and *Aedes aegypti* are the 2 main mosquito species competent for transmission of chikungunya virus and are also responsible for transmission of dengue virus, another emerging vector-borne illness. *Aedes* mosquitos are notorious daytime biters and between the 2 *Aedes* species, *Aedes albopictus* can survive at more temperate latitudes and is therefore more widespread throughout the Southeast United States.

Other less commonly reported routes of infection, which have primarily been documented in regions endemic for chikungunya virus, include bloodborne transmission through needle sticks and in utero transmission, most often occurring during the antepartum period of pregnancy.

Mosquitoes become infected when they feed on a person infected with chikungunya virus. Monkeys, and possibly other wild animals, may also serve as reservoirs of the virus. Infected mosquitoes can then spread the virus to other humans when they bite. *Aedes aegypti* (also known as the yellow fever mosquito), a household container breeder and aggressive daytime biter which is attracted to humans, is the primary vector of chikungunya virus to humans. *Aedes albopictus* (also known as the Asian tiger mosquito) may also play a role in human transmission in Asia, and various forest-dwelling mosquito species in Africa have been found to be infected with the virus.

Diagnosis and Public Reporting, Chikungunya virus infection should be considered in patients with acute onset of fever and polyarthralgia, especially travelers who recently returned from areas with known virus transmission. The differential diagnosis of chikungunya virus infection varies based on place of residence, travel history, and exposures. Dengue and chikungunya viruses are transmitted by the same mosquitoes and have similar clinical features. The two viruses can circulate in the same area and can cause occasional co-infections in the same patient. Chikungunya virus infection is more likely to cause high fever, severe arthralgia, arthritis, rash, and lymphopenia, while dengue virus infection is more likely to cause neutropenia, thrombocytopenia, hemorrhage, shock, and death. It is important to rule out dengue virus infection because proper clinical management of dengue can improve outcome. In addition to dengue, other considerations include leptospirosis, malaria, *rickettsia*, group. A *streptococcus*, rubella, measles, parvovirus, enteroviruses, adenovirus, other alphavirus infections (e.g., Mayaro, Ross River, Barmah Forest, O'nyong-nyong, and Sindbis viruses), post-infections arthritis, and rheumatologic conditions.

Preliminary diagnosis is based on the patient's clinical features, places and dates of travel, and activities. Laboratory diagnosis is generally accomplished by testing serum or plasma to detect virus, viral nucleic acid, or virus-specific immunoglobulin M and neutralizing antibodies.

Chikungunya virus disease is a nationally notifiable condition. Healthcare providers are encouraged to report suspected chikungunya cases to their state or local health department to facilitate diagnosis and mitigate the risk of local transmission.

Treatment:

There are no specific treatments for chikungunya. There is no vaccine currently available. Chikungunya is treated symptomatically, usually with bed rest, fluids, and medicines to relieve symptoms of fever and aching such as ibuprofen, naproxen, acetaminophen, or paracetamol. Aspirin should be avoided. Infected persons should be protected from further mosquito exposure during the first few days of the illness so they can not contribute to the transmission cycle.

As with the majority of mosquito-borne viral infections, there is no specific antiviral treatment for chikungunya virus. However, it is important to exclude other, more serious infections for which there is targeted treatment or alternative clinical interventions available, including malaria and dengue virus, respectively.

Treatment of patients with chikungunya virus infection is entirely supportive, resigned to rest, fluids, and pain and fever management. Individuals who have persistent joint pain may require additional supportive care including corticosteroids and/or physiotherapy.

Unfortunately, Chloroquine is gaining ground as a possible treatment for the symptoms associated with chikungunya, and as an anti-inflammatory agent to combat the arthritis associated with chikungunya virus. A University of Malaya study found that for arthritis-like symptoms that are not relieved by aspirin and non-steroidal anti-inflammatory drugs (NSAID), chloroquine phosphate (250 mg/day) has given promising results. There is a debate about the appropriateness of chloroquine as treatment for chikungunya. Unpublished studies in cell culture and monkeys show no effect of chloroquine treatment on reduction of chikungunya disease.

As in our prior U.S. patent application Ser. No. 13/660,553 filed Oct. 25, 2012, now U.S. Pat. No. 9,011,892, which claims the benefit of priority to U.S. Provisional Patent Application Ser. No. 61/550,969 filed Oct. 25, 2012, we had demonstrated and listed ad nauseam the ill side effects, psychological and physical dangers of using Quinine and it's many derivatives. Once again (primarily due to it's low cost, remaining high stock counts, and the wrongful but familiar use for many years), we seem to be content traveling down that dark path once again.

In summary, chikungunya virus is an emerging, vector-borne threat to the Americas, including the United States where we have both a large naïve host population and widespread distribution of transmission competent *Aedes* species mosquitos.

Infection with chikungunya virus is typically severe presenting with high fever, polyarthralgia, and often a maculopapular rash. Diagnosis is based on clinical suspicion supported by serologic findings and/or PCR and, unfortunately, care is largely supportive only.

Table XA shows a table for the preventative composition for adults in mg per pill, and the dosing required, for the treatment of chikungunya:

TABLE XA

Preventative Composition for Adults in mg per pill
(2 capsules = 1 dosing configuration)

| Adult Dosing [mg/Pill] | Component Preventative | | | |
| --- | --- | --- | --- | --- |
| | Broad Range | Preferred Range | Preferred Amount | Substitution Category |
| ACTIVE INGREDIENTS | | | | |
| artemisinin | 25-60 mg | 45-55 mg | approx 50 mg | |
| berberine | 175-500 mg | 300-450 mg | approx 400 mg | |
| capsaicin | 150-300 mg | 200-275 mg | approx 225 mg | |
| Papaya Leaf extract | 20-80 mg | 30-50 mg | approx 60 mg | |
| The following two categories (Blended Mixture and Inert ingredients) are only used when making a compressed pill | | | | |
| BLENDED MIXTURE* | 0-500 mg | 300-500 mg | approx 350 mg | Excipient with Active Ingredients |
| INERT INGREDIENTS | For binding or delivery of other ingredients. | | | |
| microcrystalline cellulose | 0-650 | 400-650 | approx 540 | Binders and compaction |
| stearic acid | 0-200 | 200-400 | approx 300 | Lubricant excipient |
| silicon dioxide | 0-50 | 30-50 | approx 40 | Water reducing agent and to promote absorption of water and prevent caking and clumping |

TABLE XA-continued

Preventative Composition for Adults in mg per pill
(2 capsules = 1 dosing configuration)

| Adult Dosing [mg/Pill] | Component Preventative | | | |
|---|---|---|---|---|
| | Broad Range | Preferred Range | Preferred Amount | Substitution Category |
| calcium carbonate | 0-1100 | 800-1100 | approx 1000 | Inert filler |
| magnesium stearate | 0-90 | 60-90 | approx 75 | For lubricating properties and to prevent powdered component from sticking to the pill press equipment during the compression from powder into solid tablets |
| croscarmellose sodium | 0-50 | 35-50 | approx 40 | To reduce water solubility and allow the material to expand, absorbing many times its weight in water and removing much of the water from Berberine. |

Approximately is defined as +/−5% in order to cover manufacturing variances and dosing tolerances.

In the tables, a gel cap example can consist of only artemisinin, berberine, capsaicin, and papaya extract in the amounts referenced in the above tables.

The inert ingredients are not therapeutic and are designed for the integrity, palatability and stability of the tablets. There are many substitutes for the various classes of inert ingredients that can include disintegrants, lubricants, binders and excipients.

Disintegrants can include but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating Agents or Desiccating Agents can include but are not limited to sodium carboxy methyl cellulose, silica gel, microcrystalline cellulose, carboxymethylcellulose calcium, cellulose, colloidal silicone dioxide, and crosscarmellose sodium.

*The blended mixture referenced can include a blended mixture approximately 400 mg of concentrate of black walnut (*Juglans nigra*) dry outer hull; approximately 500 mg of concentrate of organically grown wormwood (*Artemisia absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

For adults, defined as persons with a body weight of at least 110 pounds, two capsules per day with a meal is taken for 7 to 14 days depending on the number of days desired to stay parasite free. Two capsules per day for 7 to 14 days is effective for preventing infection for 30 to 60 days, respectively.

Table XB covers a dose per body weight (in mg per kg) for customizing dosages for adults less than or greater than 180 pounds (81.65 kgs), for the treatment of chikungunya:

TABLE XB

DOSE PER BODY WEIGHT FOR ADULTS (mg per kg)

| Adult Dosing [mg/kg] | Component Preventative | | | |
|---|---|---|---|---|
| | Broad Range mg/kg | Preferred Range mg/kg | Preferred Amount mg/kg | Substitution Category mg/kg |
| ACTIVE INGREDIENTS | | | | |
| artemisinin | 22.68-54.43 | 40.82-49.89 | approx 45.36 | |
| berberine | 158.76-453.60 | 272.15-408.23 | approx 362.87 | |
| Capsaicin | 68.18-136.36 | 90.91-125.00 | 102.27 | |
| Papaya Leaf Extract | 9.09-36.36 | 13.64-22.73 | 27.27 | |
| THE TWO CATEGORIES BELOW ARE USED ONLY IF MAKING COMPRESSED PILL | | | | |
| BLENDED MIXTURE* | 0-226.80 | 136.08-226.80 | approx 158.76 | Excipient with Active Ingredients |
| INERT INGREDIENTS | For binding or delivery of other ingredients. | | | |
| microcrystalline cellulose | 0-294.83 | 181.94-294.83 | approx 244.94 | Binders and compaction |
| stearic acid | 0-181.44 | 90.72-181.44 | approx 136.08 | Lubricant excipient |
| silicon dioxide | 0-22.68 | 13.61-22.68 | approx 18.14 | Water reducing agent and to promote absorption of water and prevent caking and clumping |
| calcium carbonate | 0-498.95 | 362.89-498.95 | approx 453.59 | Inert filler |
| magnesium stearate | 0-40.82 | 27.22-40.82 | approx 34.02 | For lubricating properties & to prevent powdered component from sticking to pill press equipment during compression from powder into solid tablets |
| croscarmellose sodium | 0-22.68 | 15.88-22.68 | approx 18.14 | To reduce water solubility and allow the material to expand, absorbing many times its weight in water and removing much of the water from Berberine. |

Approximately is defined as +/−5% in order to cover manufacturing variances and dosing tolerances.

For adults, defined as persons above the age of 12 with a body weight above 110 pounds, adult's dosage size is two tablets; thereby providing approximately 100 mg artemisinin per dosage. Tablets must be ingested through the mouth. Directions for taking the anti-chikungunya formula are as follows:

Day 1—Take two tablets in the morning
    Take two tablets in the evening
Day 2—Take two tablets in the morning
    Take two tablets in the evening
Day 3—Take two tablets in the morning
Day 4—Take two tablets in the morning The four-day dosage regimen outlined above as an anti-chikungunya treatment requires the consumption of a total of 12 tablets over a consecutive four-day period.

In the tables, a gel cap example can consist of only artemisinin, berberine, capsaicin, and papaya extract in the amounts referenced in the above tables.

*The blend mixture can consist of a blended mixture approximately 400 mg of concentrate of black walnut (*Juglans nigra*) dry outer hull; approximately 500 mg of concentrate of organically grown wormwood (*Artemisia*

*absinthium*) dry flower and leaf; approximately 150 mg of concentrate of Clove (*Syzygium aronalicum*) dry flower; and approximately 700 mg of fresh leaf organically grown Chinese wormwood (*Artemisia annua*).

The concentrate of black walnut is an astringent that supports the intestinal system. Organically grown wormwood is used to improve appetite, aid in digestive functions, and assist in the absorption of nutrients. The concentrate of Clove is a carminative, to increase hydrochloric acid in the stomach and to improve peristalsis. Chinese wormwood is used to reduce and stop fever.

The inert ingredients are not therapeutic and are designed for the integrity, palatability and stability of the tablets. There are many substitutes for the various classes of inert ingredients that can include disintegrants, lubricants, binders, and excipients. The following classes can include but are not limited to:

Disintegrants can include but are not limited to guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating agents or Desiccating Agents can include but are not limited to sodium carboxy methyl cellulose, silica gel, microcrystalline cellulose, carboxymethylcellulose calcium, cellulose, colloidal silicone dioxide, and crosscarmellose Sodium.

Approximately is defined as +/−5% in order to cover manufacturing variances and dosing tolerances.

In the tables, a gel cap example can consist of only artemisinin, berberine, capsaicin, and papaya extract in the amounts referenced in the above tables.

Thus, someone skilled in the art makes a judicious selection of an appropriate dosage regimen; selection is dependent on the age or body weight of the patient, condition to be treated and the judicious selection is not a limitation of the present invention.

Table XIA lists the treatment composition for children in mg per pill for the treatment of chikungunya (two pills equals dosage).

TABLE XIA

Treatment Composition for Children in mg per pill

| Children's Dosing (mg/Pill) | Broad Range | Preferred Range | Preferred Amount | Substitution Category |
|---|---|---|---|---|
| ACTIVE INGREDIENTS | | | | |
| artemisinin | 12.5-30 mg | 22.5-27.5 mg | approx 25 mg | |
| berberine | 87.5-250 mg | 150-225 mg | approx 200 mg | |
| Capsaicin | 75-150 mg | 100-138 mg | approx 115 mg | |
| Papaya Leaf Extract | 20-80 mg | 30-50 mg | approx 60 mg | |
| The following ingredients, both inactive and inert, are only used when making a compressed pill INACTIVE INGREDIENTS | | | | |
| peppermint | 0-70 mg | 35-70 mg | approx 50 mg | flavoring |
| xylitol | 0-1,200 mg | 800-1,200 mg | approx 1,000 mg | sweetener |
| 83% maltodextrin & 17% natural flavors | 0-120 mg | 80-120 mg | approx 100 mg | Masking agent |
| sucralose | 0-12 mg | 8-12 mg | approx 10 mg | Sweetener. For binding or delivery of other ingredients |
| INERT INGREDIENTS | | | | |
| Silicon dioxide | 0-220 mg | 160-220 mg | approx 200 mg | Water reducing agent that promotes absorption of water & prevents caking or clumping |
| Calcium carbonate | 0-1,200 mg | 800-1,200 mg | approx 1,000 mg | Inert filler |
| Precipitated silica | 0-29 mg | 23-29 mg | approx 26.66 mg | Anticaking free flow agent |

Approximately is defined as +/−5% in order to cover manufacturing variances and dosing tolerances.

For children, defined as persons between the ages of 2 and 12 with a body weight below 110 pounds, children's dosage size is two tablets; thereby providing approximately 50 mg artemisinin per dosage. Tablets can be ingested through the mouth. Directions for taking the anti-chikungunya formula can be as follows:

Day 1—Take two tablets in the morning
Take two tablets in the evening
Day 2—Take two tablets in the morning
Take two tablets in the evening
Day 3—Take two tablets in the morning
Day 4—Take two tablets in the morning The four-day dosage regimen outlined above as an anti-chikungunya treatment requires the consumption of a total of 12 tablets over a consecutive four-day period.

In the tables, a gel cap example can consist of only artemisinin, berberine, capsaicin, and papaya leaf extract in the amounts referenced in the above tables.

The inert ingredients are not therapeutic and are designed for the integrity, palatability and stability of the tablets. There are many substitutes for the various classes of inert ingredients that can include disintegrants, lubricants, binders, excipients Disintegrants can include guar gums, ion exchange resins, gums, micro-crystalline cellulose, aginates, cellulose, starches, sodium starch glycolate, cross povidone, gum karaya, chitin and chitosan, smecta, gullan gums, isapghula husk, polacrillan potassium, and agar.

Lubricants can include but are not limited to stearic acid, magnesium stearate, silica, hydrogenated vegetable oil, mineral oil, polyethylene glycol, glyceryl palmitostearate, glyceryl bahenate, sodium benzoate, sodium stearyl fumarate, talc, and silicon dioxide.

Binders can include but are not limited to acacia, alginic acid, aluminum hydroxide, calcium hydroxide, calcium oxide, carboxymethyl cellulose, cellulose, ethyl cellulose, gelatin, guar gum, maltodextrin, methyl cellulose, polyethylene glycol, and povidone.

Excipients can include but are not limited to flavorings, cellulose derivatives, calcium carbonate, magnesium stearate, silicon dioxide, masking agents, saccharides and their derivatives, gelatin, synthetic polymers, coatings and enterics, fillers and stearates.

Dehydrating Agents or Desiccating Agents can include but are not limited to sodium carboxy methyl cellulose, silica gel, microcrystalline cellulose, carboxymethylcellulose calcium, cellulose, colloidal silicone dioxide and crosscarmellose sodium.

Table XIB covers a dose per body weight (in mg per kg) for customizing dosages for children having weights of less than 100 pounds (45.36 kgs) for the treatment of chikungunya:

TABLE XIB

| | DOSE PER BODY WEIGHT FOR CHILDREN (mg per kg) | | | |
|---|---|---|---|---|
| | Component | | | |
| Children's Dosing | Broad Range mg/kg | Preferred Range mg/kg | Preferred Amount mg/kg | Substitution Category |
| ACTIVE INGREDIENTS | | | | |
| artemisinin | 5.67-13.61 | 10.21-12.47 | approx 11.39 | |
| berberine | 39.69-113.40 | 68.04-102.06 | approx 90.72 | |
| Capsaicin | 34.09-68.18 | 45.45-62.73 | approx 52.27 | |
| Papaya Leaf extract | 4.55-18.20 | 6.82-11.36 | approx 13.64 | |
| The following ingredients, both inactive and inert only used when making a compressed pill | | | | |
| INACTIVE INGREDIENTS | | | | For binding or delivery of other ingredients |
| peppermint | 0-31.75 | 15.88-31.75 | approx 22.68 | flavoring |
| xylitol | 0-544.31 | 362.87-544.31 | approx 453.60 | Sweetener |
| 83% maltodextrin & 17% natural flavors | 0-54.43 | 36.29-54.43 | approx 45.36 | Masking agent |
| sucralose | 0-5.44 | 3.63-5.44 | approx 4.54 | Sweetener |
| INERT INGREDIENTS | | | | For binding or delivery of other ingredients |
| Silicon dioxide | 0-99.79 | 72.57-99.79 | approx 90.72 | Water reducing agent that promotes absorption of water & prevents caking or clumping |
| Calcium carbonate | 0-544.31 | 362.87-544.31 | approx 453.60 | Inert filler |
| Precipitated silica | 0-13.15 | 10.43-13.15 | approx 12.09 | Anticaking, free flow agent |

Approximately is defined as +/−5% in order to cover manufacturing variances and dosing tolerances.

In the tables, a gel cap example can consist of only artemisinin, berberine, capsaicin, and papaya leaf extract in the amounts referenced in the above tables.

For children, defined as persons between the ages of 2 and 12 with a body weight below 110 pounds, children's dosage size is two tablets; thereby providing approximately 50 mg artemisinin per dosage. Tablets must be ingested through the mouth. Directions for taking the anti-chikungunya formula are as follows:

Day 1—Take two tablets in the morning
Take two tablets in the evening
Day 2—Take two tablets in the morning
Take two tablets in the evening
Day 3—Take two tablets in the morning
Day 4—Take two tablets in the morning The four-day dosage regimen outlined above as an anti-chikungunya treatment requires the consumption of a total of 12 tablets over a consecutive four-day period.

Methods of Manufacturing Tablets, Pills and Capsules

Our product by design and claim states a "passively accurate dosing system." Our manufacturing claims stated herein make it extremely possible to maintain and honor those claims. However, one can never preclude the possibility of the existence of some variance when mixing powdered compounds under high pressure. Although the FDA (stated in a 2004 letter from Dr. Steven Galson, then director of the Center for Drug Evaluation and Research at the FDA and now U.S. Surgeon General, that −20/+25%, "actually represents the acceptable bounds on the 90% confidence intervals around the ratio of the mean result for products") accepts those high deviations as normal, our concern was for tolerances at those extreme limits. However, while we believe there to be a reasonable amount of efficacy and safety at these extremes; we do not expect to exceed plus or minus 5% of our stated ingredient values.

Before the two active ingredient raw materials are accepted by the manufacturing laboratory, a chemical analysis of the composition is performed by an independent, third party commercial laboratory. This analysis confirms the purity of the materials as well as other compounds that might be present in the shipment. Industry standards for purity and other compounds are known and used to accept or reject a shipment.

Once the product is manufactured but before it is packaged, random batch samples are sent to another independent, third party commercial analysis laboratory where the pills are inspected and broken down to determine their contents. The dosing amounts are maintained as stated on the packaging, and the pills must be free of any contaminants. Failure to obtain the analysis laboratory approval results in a rejection of the batch.

In the Examples below, two types of compounds previously identified as anti-malarial agents are combined into one single pill along with capsaicin and Papaya Leaf extract. Artemisinin is a plant-based terpenoid compound that is known for use as an anti-malarial agent. Berberine is a plant-based alkaloid with a very bitter taste and water content in a range of approximately 14 wt. %. Successful bonding and adhesion through use of non-active ingredients is essential in order to produce a compressed physically stable pill. Adding granulation steps to the process reduces water and subsequently reduces the amount of non-active ingredients or excipients needed.

In addition, the manufacturing process solves the problem of keeping the formulated pill from becoming hydrated during shipment and storage in tropical climates by using blister packing immediately at the end of processing to maintain chemical composition and stability.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. An artemisinin and berberine treatment composition for treating a patient in a single pill, tablet or capsule consisting of, in combination:
   artemisinin;
   berberine;
   capsaicin;
   Papaya Leaf extract; and
   at least one binding or delivery component, wherein the composition is in a single pill, tablet or capsule, for the treatment of chikungunya.

2. The composition of claim 1, wherein the composition is adaptable for an adult patient for the treatment of chikungunya, and consists of:
   25-60 mg artemisinin;
   175-500 mg berberine;
   150-300 mg capsaicin;
   20-80 mg Papaya Leaf extract; and
   the at least one binding or delivery component, wherein the composition is in a single pill, tablet or capsule, for the treatment of chikungunya.

3. The composition of claim 2, wherein the composition is adaptable for an adult patient for the treatment of chikungunya, and consists of:
   45-55 mg artemisinin;
   400-450 mg berberine;
   200-275 mg capsaicin;
   30-50 mg Papaya Leaf extract; and the at least one binding or delivery component, wherein the composition is in a single pill, tablet or capsule, for the treatment of chikungunya.

4. The composition of claim 3, wherein the composition is adaptable for an adult patient for the treatment of chikungunya, and consists of:
   approximately 50 mg artemisinin;
   approximately 400 mg berberine;
   approximately 225 mg capsaicin; and
   approximately 60 mg Papaya Leaf extract; and the at least one binding or delivery component, wherein the composition is in a single pill, tablet or capsule, for the treatment of chikungunya.

5. The composition of claim 2, wherein the composition is adaptable for an adult patient for the treatment of chikungunya, wherein the at least one binding or delivery component consists of:
   at least one ingredient selected from at least one of: microcrystalline cellulose, stearic acid, silicon dioxide, calcium carbonate, magnesium stearate, and croscarmellose sodium.

6. The composition of claim 1, wherein the composition is adaptable for an adult patient for the treatment of chikungunya, in mg/kg and consists of:
   22.68-54.43 mg/kg artemisinin;
   158.76-453.60 mg/kg berberine;
   68.18-136.36 mg/kg capsaicin;

9.09-36.36 mg/kg Papaya Leaf extract; and the at least one binding or delivery component, wherein the composition is in a single pill, tablet or capsule, for the treatment of chikungunya.

7. The composition of claim 6, wherein the composition is adaptable for an adult patient for the treatment of chikungunya, in mg/kg and consists of:
- 40.82-49.89 mg/kg artemisinin;
- 272.15-408.23 mg/kg berberine;
- 90.91-125 mg/kg capsaicin;
- 13.64-22.73 mg/kg Papaya Leaf extract; and the at least one binding or delivery component, wherein the composition is in a single pill, tablet or capsule, for the treatment of chikungunya.

8. The composition of claim 7, wherein the composition is adaptable for an adult patient for the treatment of chikungunya, in mg/kg and consists of:
- approximately 45.36 mg/kg artemisinin;
- approximately 362.87 mg/kg berberine;
- approximately 102.27 mg/kg capsaicin;
- approximately 27.27 mg/kg Papaya Leaf extract; and the at least one binding or delivery component, wherein the composition is in a single pill, tablet or capsule, for the treatment of chikungunya.

9. The composition of claim 6, wherein the composition is adaptable for an adult patient for the treatment of chikungunya, and the at least one binding or delivery component consists of:
- at least one ingredient selected from at least one of: microcrystalline cellulose, stearic acid, silicon dioxide, calcium carbonate, magnesium stearate, and croscarmellose sodium.

10. The composition of claim 1, wherein the composition is adaptable for a child patient for the treatment of chikungunya, and consists of:
- 12.5-30 mg artemisinin;
- 87.5-250 mg berberine;
- 75-250 mg capsaicin;
- 20-80 mg Papaya Leaf extract; and the at least one binding or delivery component, wherein the composition is in a single pill, tablet or capsule, for the treatment of chikungunya.

11. The composition of claim 10, wherein the composition is adaptable for a child patient for the treatment of chikungunya, and consists of:
- 22.5-27.5 mg artemisinin;
- 150-225 mg berberine;
- 100-138 mg capsaicin;
- 30-50 mg Papaya Leaf extract; and the at least one binding or delivery component, wherein the composition is in a single pill, tablet or capsule, for the treatment of chikungunya.

12. The composition of claim 11, wherein the composition is adaptable for a child patient for the treatment of chikungunya, and consists of:
- approximately 25 mg artemisinin;
- approximately 200 mg berberine;
- approximately 115 mg capsaicin;
- approximately 60 mg Papaya Leaf extract; and the at least one binding or delivery component, wherein the composition is in a single pill, tablet or capsule, for the treatment of chikungunya.

13. The composition of claim 10, wherein the composition is adaptable for a child patient for the treatment of chikungunya, wherein the at least one binding or delivery component consists of:
- at least one ingredient selected from at least one of: peppermint, xylitol, maltodextrin and natural flavors, and sucralose.

14. The composition of claim 10, wherein the composition is adaptable for a child patient for the treatment of chikungunya, wherein the at least one binding or delivery components consists of:
- at least one ingredient selected from at least one of: silicon dioxide, calcium carbonate, and precipitated silica.

15. The composition of claim 1, wherein the composition is adaptable for a child patient for the treatment of chikungunya in mg/kg, and consists of:
- 5.67-13.61 mg/kg artemisinin;
- 39.69-113.40 mg/kg berberine;
- 34.09-68.18 mg/kg capsaicin;
- 4.55-18.20 mg/kg Papaya Leaf extract; and the at least one binding or delivery component, wherein the composition is in a single pill, tablet or capsule, for the treatment of chikungunya.

16. The composition of claim 15, wherein the composition is adaptable for a child patient for the treatment of chikungunya in mg/kg, and consists of:
- 10.21-12.47 mg/kg artemisinin;
- 68.04-102.06 mg/kg berberine;
- 45.45-62.73 mg/kg capsaicin;
- 6.82-11.36 mg/kg Papaya Leaf extract; and the at least one binding or delivery component, wherein the composition is in a single pill, tablet or capsule, for the treatment of chikungunya.

17. The composition of claim 16, wherein the composition is adaptable for a child patient for the treatment of chikungunya in mg/kg, and consists of:
- approximately 11.39 mg/kg artemisinin;
- approximately 90.72 mg/kg berberine;
- approximately 52.27 mg/kg capsaicin;
- approximately 13.64 mg/kg Papaya Leaf extract; and the at least one binding or delivery component, wherein the composition is in a single pill, tablet or capsule, for the treatment of chikungunya.

18. The composition of claim 15, wherein the composition is adaptable for a child patient for the treatment of chikungunya, wherein the at least one binding or delivery component consists of:
- at least one ingredient selected from at least one of: peppermint, xylitol, maltodextrin and natural flavors, and sucralose.

19. The composition of claim 15, wherein the composition is adaptable for a child patient for the treatment of chikungunya, wherein the at least one binding or delivery component consists of:
- at least one ingredient selected from at least one of: silicon dioxide, calcium carbonate, and precipitated silica.

20. An artemisinin and berberine treatment composition consisting of:
- artemisinin;
- berberine;
- capsaicin;
- Papaya Leaf extract; and
- at least one binding or delivery component.

* * * * *